United States Patent [19]
Amory et al.

[11] Patent Number: 5,264,350
[45] Date of Patent: Nov. 23, 1993

[54] DNA SEQUENCE PERFORMING A FUNCTION WHICH IS EXPRESSED IN AN OVER-PRODUCTION OF EXTRACELLULAR PROTEINS BY VARIOUS STRAINS OF BACILLUS, AND VECTORS CONTAINING THIS SEQUENCE

[75] Inventors: Antoine P. Amory, Voisins-le-Bretonneux; Georges Rapoport, Paris; Frederik Kunst, Ivry-sur-Seine; André Klier, Neuilly-sur-Marne; Raymond Dedonder, Chatenay-Malabry, all of France

[73] Assignee: Institut Pasteur, France

[21] Appl. No.: 798,366

[22] Filed: Nov. 21, 1991

Related U.S. Application Data

[63] Continuation of Ser. No. 186,478, Jun. 26, 1988, filed as PCT/FR87/00323, Aug. 18, 1987, abandoned.

[30] Foreign Application Priority Data

Aug. 18, 1986 [FR] France .................... 86 11826

[51] Int. Cl.$^5$ .................... C12P 21/00; C12P 21/02; C12N 15/00; C12N 15/31; C12N 15/75; C07K 7/00
[52] U.S. Cl. .................... 435/69.1; 435/252.31; 435/320.1; 530/324; 536/23.4; 536/23.7; 935/33; 935/47; 935/48
[58] Field of Search .................... 530/324; 435/69.1–69.9, 71.1–71.3, 172.1, 172.3, 320.1, 252.3–252.35; 536/27, 23.4, 23.7; 935/33, 47–51

[56] References Cited

PUBLICATIONS

Yang et al; J. Bacteriol. 166: 113 (1986).
Yang et al; J. Bacteriol. 167: 1098 (1986).
Chang et al, in Molecular Cloning and Gene Regulation in Bacilli, 1982, Ganesan et al (ed.), Academic Press, New York, pp. 159–169.

*Primary Examiner*—James Martinell
*Attorney, Agent, or Firm*—Burns, Doane, Swecker & Mathis

[57] ABSTRACT

The invention relates to any fragment of DNA derived from the genome of *B. licheniformis* coding for a polypeptide of 46 amino acids, or for any fragment of this polypeptide possessing the property of stimulating the production of enzymes secreted by *B. subtilis* by introduction of the above-mentioned fragment of DNA into this latter by the intermediary of a plasmid.

The invention also relates to a procedure for the stimulation of the production of a specific polypeptide by *B. subtilis* by introduction of the above-mentioned fragment of DNA in a strain of *B. subtilis*, the genome of which has been modified so that it contains a sequence of DNA coding for the said specific polypeptide.

25 Claims, 15 Drawing Sheets

```
       EcoRI
         Sma
▨▨▨GATCGAATGAGACGATCAAGCTGGCTGCGGACGCCGGTTTGCCTGAGCGCGGCCAGCACG

TTATTTTTTTGGTTGCTTTGGGCAGCCGTCATGATTTGCTGGGCCAAAGTACGCCAGGCT
                     .         .       100       .         .
      GAAAGCCTGCTTAAAATTCTCTGTCCGTCAGCCATCAAGCTCTCCGCTTCTTTTGCCGAG
          .         .         .         .         .         .
      CGCAATAAGGCGGCTGACTTGAACTTCGGGATAGACCTGCCGGCAGCTGACGTGTTGATA
                     200       .         .  PvuII   .         .
      TGGATGCATCCAAAAGCAATGAGGAGGAAGCAATATGAACACCTCTTTTCAATTTTTACG
          .         .         .         .         .       300
      GGTCAAATTGCGGTTTTTGCGGTGTAAGGCGAAGGGATGGTTTTTTATAAGGGCCGAAAT
                     .         .         .  HaeIII   .         .
      GCGTGTCGGTCTATTGCGTGTTTTTCGGTGGCGCATACCCGATCTGCGTTCCGTGAACAC
          .         .         .       400       .         .
      TCAAGTTTTTCTATTCCTCGCTAGTTACTACTTTAGACTCAAGGTTGCAAAACGAACAAA
                     .         .         .         .         .
      ACACAACTGAACTTGCGATGATAAAGGGGTTTATATGCGATCTTTATTTGACTCCTTGAA
          .       500       .         .         .         ↑__.
      AAACAAACAAAAATTTTATGTTTCATTAGGATTTGAGAACTAATCGCAAGTTGTGTAAAA
                     .         .         .         .       600
      TGGGTGTTATGGTCTATTTAAAGTTTGCGGTGTAACGCATGAATTTATATGCAACTTTTC
          .         .         ↑__.        .         .         .
      GGTGAAAAAGAAACCAAATCCCTTTAAACTTGTATTAACAGATCAAATACCTATGACTCG
      HphI   .         .  AhaIII .        700       ↑__.

fMetGluLysGlnG
      TTCACTATACACAAATTGATTGATCTTCCAAAAGGAGTGTGGAACCGGTGGAAAAGCAAC
          .         .        'Sau3AI'   .         .         .
      lnIleGluGluLeuLysGlnLeuLeuTrpArgLeuGluAsnGluIleArgGluThrLysAs
      AAATTGAAGAATTAAAACAACTGCTTTGGCGGCTAGAGAATGAAATCAGAGAAACAAAGG
                     .       800       ↑__.        .         .

FIG. 3A
```

```
        SerLeuArgLysIleAsnLysSerIleAspGlnTyrAspLysTyrThrTyrLeuLysT
        ACTCCTTGCGCAAGATTAACAAAAGCATTGATCAATACGATAAGTACACATATCTAAAAA
                 .         .         .         .  RsaI   .        900 hrSer
CCTCGTAAAAAGACTTGTTTCAGACAAGTCTTTTTTTTGTGTGCAAACGAACCCAAAAAA
         .         .         .         .         .         .

AGGATAAATTATTATATAATTGTTAAATAAAAAAATTGCTCTGTCAATCGGGATTTTGAT
         .         .         .        1000        .         .

TTAGTAAAATATTAAGAAAGGAGGGAGCACCATCTCTAAGCTTTTTTGTCTAGATCACAG
         .         .         .       ·HindIII     .         .

TAAAATCAAGCAAAGAATGAATCATTTTATAGACCTTGAGATTCCCAATGCGGACTTAAA
         .       1100        .         .         .         .

TCGGACGCTGCACGCTTTTCTAGATGCAAAGGACCAGTTGCATTTCAGCGAGCTTGCTTT
         .         .         .         .        1200

TTATCATTACCAAAGTTTCGGCGGCACGGACACCGATGCGGCAGAAACCCTTGGAGCAGG
         .         .         .         .         .         .

CATTGAACTCTTGATTCTTGCGTTTGATATATTCGATGATTTAGAGGATGAAGACAGCCC
         .         .         .       1300        .         .

CGATGAACCTTGGATGAAAATCAACCGTTCAGTCGCAATGAATGCGGCGACTGCGCTTTA
         .         .         .         .         .         .

TACAATAAGCATTAAAGT
         .      SalI    PstI     HindIII
```

```
                      5                   10                  15
B.s.    Met Glu Lys Lys Leu Glu Glu Val Lys Gln Leu Leu Phe Arg Leu Glu
B.a.    ——— ——— ——— ——— ——— ——— ——— ——— Gln Gln ——— Leu ——— ——— ——— ———
                                                 Ile
B.l.    ——— ——— ——— ——— ——— ——— ——— ——— ——— ——— ——— ——— Trp ——— ——— ———

20                  25                  30
B.s.    Leu Asp Ile Lys Glu Thr Thr Asp Ser Leu Arg Asn Ile Asn Lys Ser
B.a.    ——— Asn ——— ——— Arg ——— ——— ——— ——— ——— ——— ——— ——— ——— ——— ———
B.l.    ——— Asn Glu ——— Arg ——— ——— Lys ——— ——— ——— ——— Lys ——— ——— ———

35                  40                  45
B.s.    Ile Asp Gln Leu Asp Lys Tyr Asn Tyr Ala Met Lys Ile Ser
                                                Phe Ser
B.a.    ——— ——— ——— ——— ——— ——— Tyr ——— ——— Thr ——— Leu xxx ——— Thr
B.l.    ——— ——— ——— ——— ——— ——— ——— ——— ——— ——— ——— ——— ——— ———
```

FIG.8

```
B.s. SacQh    ACTTTTCGGTGAAAAATGAGCCGAAAGCAGACACACTATTAG
B.s. SacQ+    ACTTTTCGGTGAAAAATCCCGCAAAAACGTTTACACTATTAG
B.a.          ACTTTTCGGTGAAAAAGAAACCAAATCCCTTTAAACTTGTAT
B.l.          AAATGGGCGTGAAAAAAAGCGCGATTATGTAAAATATAAA
B.s. "P43"
              "-35"                                "-10"
```

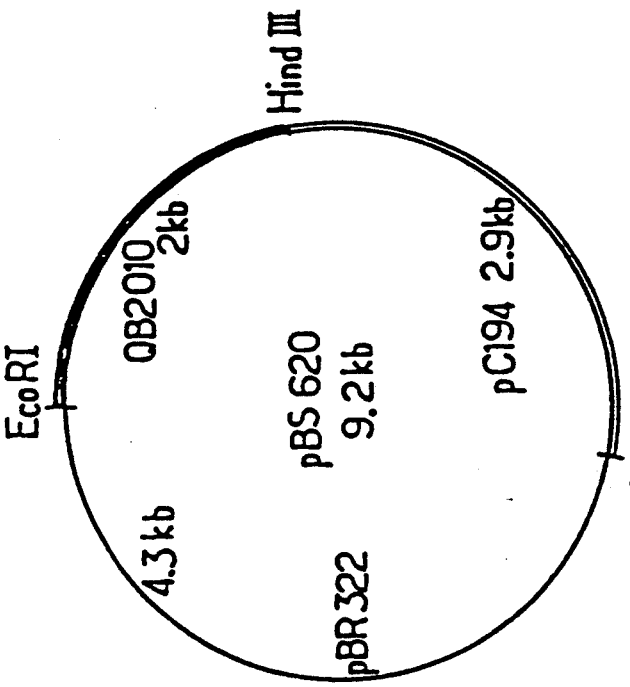
FIG. 10
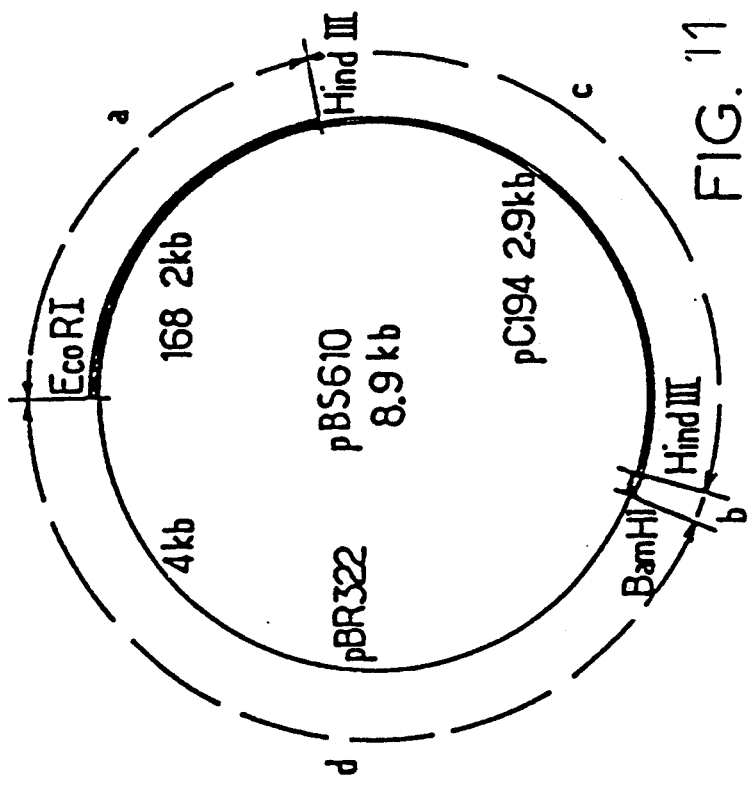
FIG. 12
FIG. 11

DNA SEQUENCE PERFORMING A FUNCTION WHICH IS EXPRESSED IN AN OVER-PRODUCTION OF EXTRACELLULAR PROTEINS BY VARIOUS STRAINS OF BACILLUS, AND VECTORS CONTAINING THIS SEQUENCE

This application is a continuation of application Ser. No. 186,478 filed Jun. 20, 1988, filed as PCT/FR87/00323, Aug. 18, 1987, now abandoned.

BACKGROUND OF THE INVENTION

In a general manner, the invention relates to a sequence of DNA performing a function which is expressed in an over-production of extracellular proteins by various strains of Bacillus, as well as vectors containing this sequence.

The invention relates more especially to a sequence of DNA coding for a polypeptide acting on the over-production of extracellular enzymes, in particular of alkaline protease, by *B. subtilis*.

In fact, the growing interest directed in recent years toward the use of *B. subtilis* as a host for cloning, and destined in particular for the production of extracellular proteins, can be explained on the following grounds. Firstly, the genetic characterization of *B. subtilis* has been carried out to a large extent, and effective methods for the introduction and extraction of DNA fragments as well as selective markers of resistance to certain antibiotics have already been described. Moreover, owing to its properties of sporulation, *B. subtilis* represents a good model of procaryotic differentiation.

From a practical point of view, one of the interesting properties of this organism is that it can be handled in complete safety because it does not infect humans or animals.

Moreover, it possesses the property of secreting a large number of enzymes (Bacteriological Reviews: 41, 711–753 (1977), some of which, such as α-amylase, proteases and glucanases, are particularly interesting at the industrial level. In particular, the alkaline protease is very much used in the manufacture of detergents as well as in the pharmaceutical industry and the agri-foodstuffs industry.

The techniques for the recombination of DNA have also made it possible to use *B. subtilis* as a host which secretes foreign proteins. In these constructions, the gene corresponding to the protein in question is fused with a sequence which allows its expression and its secretion by *B. subtilis*, the said sequence being also referred to by the expression "signal sequence" coding for a signal peptide. Numerous examples have been described which use the regulatory sequences as well as the regions corresponding to the signal peptides of α-amylase, alkaline protease and the neutral protease of *B. subtilis* (*J. Bacteriol.*, 165, 837–842, (1986)), *B. amyloliquefaciens* and *B. licheniformis*.

However, although *B. subtilis* seems to be a receptor host of choice as a result of its being well characterized, the levels of secretion for this organism are much lower if they are compared with those of Bacillus strains used in industry such as *B. licheniformis*, *B. amyloliquefaciens* or *B. stearothermophilus* which are capable of producing large amounts of secreted enzymes.

A typical example is that of alkaline protease.

The *B. subtilis* 168 strain placed in culture under laboratory conditions and in an optimal culture medium can produce 50 to 100 units of azocasein per ml of supernatant of an activity of the type of that of alkaline protease.

The industrial strain *B. licheniformis* (deposited in the National Collection of Cultures of Micro-organisms at the Pasteur Institute in Paris under the number 71 I 001) grown in that same optimal culture medium can produce more than 100,000 units of azocasein per ml, thus in a yield multiplied by a factor of 1,000.

It is possible that such strains have accumulated mutations which alter the properties of the secreted enzyme such as thermostability, and/or mutations which increase the levels of secretion and synthesis of proteins.

During recent years, detailed studies have been carried out in order to increase the production of alkaline protease in the well characterized strain of *B. subtilis* 168. In this way, a large number of mutants have been isolated which increase the secreted levels of proteolytic enzymes.

In the first instance, hpr mutants were characterized by their over-production of alkaline and neutral proteases (*J. Bacteriol.*: 112, 1026–1028 (1972)).

Sac $U^h$ mutants (Biochimie; 56, 1481–1489, (1974)), identical with pap mutants (*J. Bacteriol.*: 161, 1182–1187 (1985), and *J. Bacteriol.*: 124, 48–54, (1975)), have also been described as possessing a pleiotropic phenotype for the over-production of levansucrase, protease and α-amylase.

Furthermore, the regulatory locus nprR2 has been described as being responsible for the specific stimulation of the secretion of the neutral protease (i. *Bacteriol.*: 139, 583–590, (1979), and *J. Bacteriol.*: 119, 82–91, (1974)). However, the molecular bases of these mutations still remain unknown since it has not been possible to clone any of the mutated allelic forms of the genes implicated in the observed phenotype. That is the reason why it is very difficult to transfer these mutations to other species of Bacillus so as to increase their productive capacity.

Several research teams have recently described the cloning of DNA fragments which make possible the hypersecretion of protease in *B. subtilis*.

The Japanese patent filed on Jul. 29, 1983 by Okada et al. under the No. 60-30 685 describes a recombinant DNA containing an inserted sequence derived from the genome of a *B. licheniformis* presented as coding for a protease of this latter type of micro-organism. The authors of the patent have used this recombinant DNA to transform cultures of *Bacillus subtilis* with a view to increasing their capacity to produce alkaline and neutral proteases.

Okada et al. (*Appl. Microbiol. Biotechnol.*: 20, 406–412, (1984)) have cloned a EcoRI fragment of 3.6 kb from *B. licheniformis* which stimulates the secretion of both the neutral protease and the alkaline protease (70×), but which has only a slight effect on the enzymes of the α-amylase type (2×); the observed phenotype is conserved when a pvuII fragment of 1.25 kb and even a Sau 3A1 fragment of 0.37 kb obtained from the EcoRI fragment are cloned. The authors do not exclude the possibility that the cloned sequence belongs to a regulator gene rather than to genes coding for proteases.

Tomioka et al. (*J. Biotechnol.*: 3, 85–96, (1985)) have also described the stimulation of the secretion of neutral (10×) and alkaline (9×) proteases with a EcoRI fragment of 4 kb derived from *B. amyloliquefaciens*; it was possible to reduce this fragment to 1.75 kb containing non-identified, open-reading frames; it did not lead to stimulation of the secretion of α-amylase.

A fragment of DNA derived from *Bacillus natto* has been described as leading to an over-production of neutral and alkaline proteases and of levansucrase (J. Bacteriol.: 166, 20-29, (1986)). The authors thought it likely that a polypeptide of 60 amino acids could be responsible for the stimulation of this over-production.

Finally, the identification of the sacQ gene, a pleiotropic gene affecting the expression of a large number of genes coding for products secreted by various strains of Bacillus as well as the identification of polypeptides of 46 amino acids encoded in this sacQ gene have recently been described in *B. subtilis* (J. Bacteriol.: 166, 113-119, (1986)), and in *B. amyloliquefaciens* (J. Biotechnol.: 3, 85-96, (1985)).

SUMMARY OF THE INVENTION

It is with the aim of inducing in *B. subtilis* an over-production larger than that achieved up to now not only of alkaline proteases but also of a large number of extracellular enzymes that the authors of this patent have used a different approach from preceding ones.

In fact, the inventors have constructed a bank of genes from the chromosome of the over-producing *B. licheniformis* strain, which they have transferred to *B. subtilis*, after ligation into appropriate plasmids, and have selected the colonies of *B. subtilis* which are over-producers of proteases. In this way, they have isolated a plasmid—hereafter designated pPR4—containing a Sau3A1 insertion fragment or "insert" of 3.5 kb which confers on the host cell the property of over-production of the secreted enzymes, in particular of alkaline protease.

The reduction of this insert by partial digestion with Sau3A1 has led the inventors to isolate a fragment of 1.4 kb which, when inserted into a plasmid and introduced by the intermediary of this latter into a host cell, induces in it the same property of over-production as that previously mentioned. A typical plasmid containing this fragment of 1.4 kb and which has been used in a detailed study of this fragment has been designated pPR41. The presence of this fragment in a strain of *B. subtilis* enables the latter to produce 70 times more alkaline protease than it could beforehand, four times more of the neutral protease, and at least 50 times more of the levansucrase. It also confers on the host cell the property of over-production of other enzymes such as cellulase, or β-glucanase, xylanase and α-amylase.

BRIEF DESCRIPTION OF THE DRAWINGS

Throughout this description, reference will be made to the drawing and the photographic reproductions in which:

FIG. 7 indicates the differences between the polypeptides encoded by the sacQ gene of *B. subtilis*, *B. amyloliquefaciens* and *B. licheniformis*, respectively, FIG. 8 presents the possible structures of the promoters in the different strains of Bacillus.

FIG. 10 presents the restriction map of a HindIII-EcoRI fragment of *B. subtilis* containing the signal sequence of the levansucrase.

FIG. 11 presents the plasmid pBS610 containing the DNA fragment of FIG. 10,

FIG. 12 presents the plasmid pBS620 also containing the DNA fragment of FIG. 10.

DETAILED DESCRIPTION OF PREFERRED EMBODIMENTS

Figure 1:
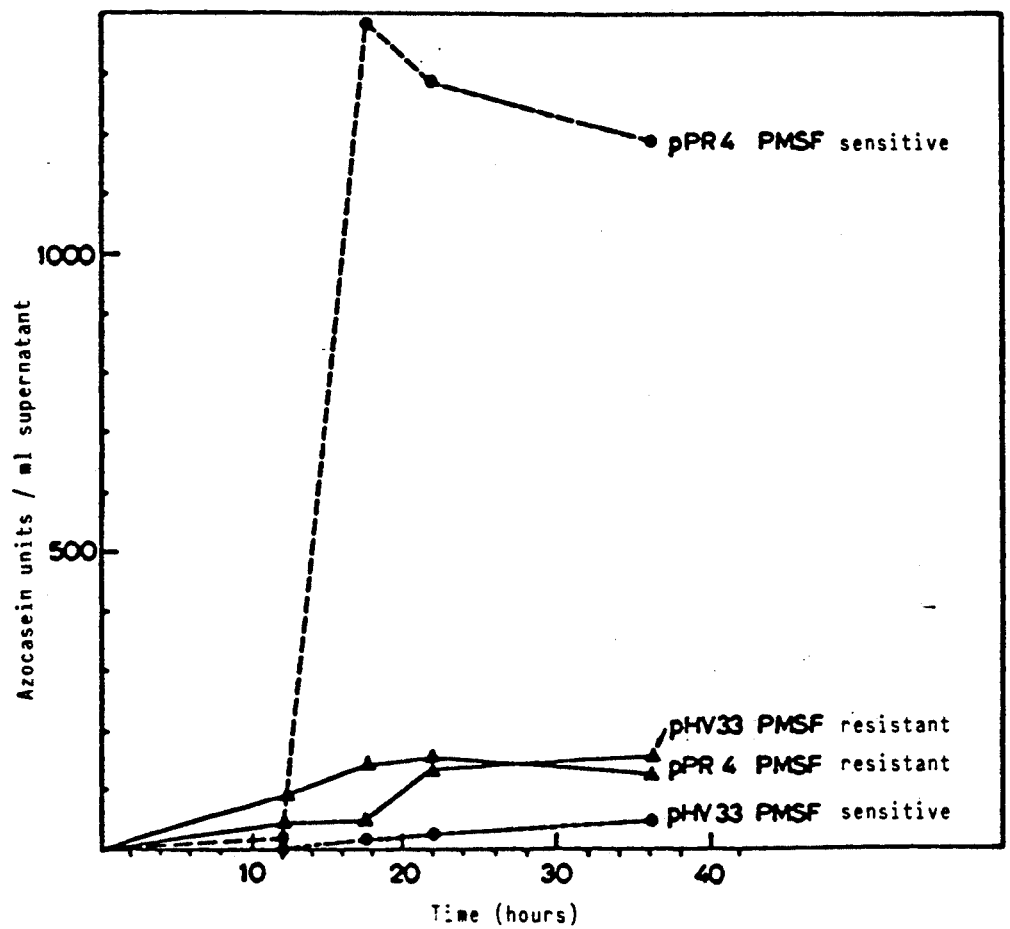
FIG. 1 is representative of the over-production of alkaline protease conferred by the plasmid pPR4 on the strain of *B. subtilis*.

The phenotype of hypersecretion conferred on the receptor strain of *B. subtilis* by the plasmid pPR41 will be designated in the ensuing discussion by the symbol $Ses^h$ (high level synthesis of secreted enzymes).

The study of the entire sequence of this DNA fragment of 1.4 kb shows that there does not exist any open-reading frame larger than 101 amino acids. The inventors have thus excluded the possibility that this DNA fragment of 1.4 kb contains the structural gene for a protease of the subtilisin type, which is composed of 379 amino acids in the form of its precursor and of 274 residues in its mature form (Nucl. Ac. Res., 13, 8913-8926, (1985)), and have attempted to reduce the size of this fragment.

The $Ses^h$ phenotype is conserved when smaller fragments derived from the 1.4 kb fragment are substituted for it in the plasmids used for the transformation of *B. subtilis*. Such smaller fragments can be obtained as the result of various deletions carried out at the 5′ and 3′ ends of the 1.4 kb fragment. It is in this way that the inventors have observed that the sequence responsible for the $Ses^h$ phenotype is contained in a fragment of 561 base pairs between the positions 353 and 914 of FIG. 3. The last 109 nucleotides of this fragment, corresponding to the positions 805 to 914, are essential but are not sufficient for the production of hypersecretion in *B. subtilis*. On the other hand, the last 228 nucleotides, corresponding to tie positions 686 to 914, are sufficient to induce the $Ses^h$ phenotype provided this fragment is preceded by a promoter of transcription recognized by *B. subtilis*. This fragment of 228 base pairs contains an open-reading frame which codes for a polypeptide of 46 amino acids and which is bounded by the nucleotide situated at the positions 768 and 905. This open-reading frame is preceded by a nucleotide sequence presumed to provide the signals characteristic of binding to the ribosome bounded by the nucleotides situated at the positions 751 and 762, and followed by a terminator of transcription bounded by the nucleotides situated at the positions 907 and 936. The inventors have also determined that the promoter of transcription is located on the fragment of 333 base pairs bounded by the nucleotides situated at the positions 353 and 686 of FIG. 3.

The polypeptide of 46 residues encoded in this fragment of 228 base pairs of *B. licheniformis* (also called polypeptide $sacQ_L$) exhibits a certain homology with the product of the gene sacQ of *B. subtilis* (or polypeptide sacQ$_S$) and *B. amyloliquefaciens* (or polypeptide sacQ$_A$) which produce the same kind of Ses$^h$ phenotype in *B. subtilis*.

However, the inventors show that the polypeptide sacQ$_L$ expressed by the corresponding nucleotide sequence incorporated into *B. subtilis* induces the phenotype (Ses$^h$) in a much more efficacious manner than does the polypeptide sacQ$_S$ or sacQ$_A$ under the same conditions. A precise determination shows that the activation of the expression of the gene for the alkaline protease is three-fold higher, whereas the activation of the sacB gene (levansucrase) is five-fold higher. This enhanced efficacity of the polypeptide of *B. licheniformis* is probably related to its primary structure.

Deletion experiments have been carried out by the inventors starting from the polypeptide sacQ$_L$ of 46 amino acids. They have thus demonstrated that the carboxyl terminal portion of the said polypeptide, and more particularly the last seven amino acids, can be modified, and even deleted, without leading to a total loss of the expression of the Ses$^h$ phenotype, and that the peptide consisting of only the first 12 amino acids is inactive.

Thus, it seems that at least a part of the residue contained between the 12th and the 39th residue of the sacQ$_L$ polypeptide and corresponding to the DNA fragment bounded by the nucleotides situated at the positions 805 and 885 of FIG. 3, is essential for the expression of the Ses$^h$ phenotype.

The enhanced expression of the Ses$^h$ phenotype following the introduction into a strain of *B. subtilis* of a vector containing a DNA sequence coding for the sacQ$_L$ polypeptide may be the result of the action on a target sequence included in the genome of *B. subtilis* of either the sacQ$_L$ polypeptide itself or of another product expressed by a part of the genome of *B. subtilis* under the control of sacQ$_L$.

The above-mentioned target sequences are generally located upstream from the structural genes coding for the enzymes secreted by *B. subtilis*.

More particularly, the inventors have characterized a target sequence contained in a fragment of 440 base pairs, bounded by the restriction sites Sau3A1-Rsa1 and located upstream from the ribosome binding site and of the DNA sequence coding for the levansucrase. This target sequence is thus located upstream from the sacB gene and comprises the sacR gene of *B. subtilis*.

The invention relates to a DNA fragment characterized by the fact that it codes for the polypeptide having the following structure:

(Nterminal)Met—Glu—Lys—Gln—Gln—

Ile—Glu—Glu—Leu—Lys—Gln—

Leu—Leu—Trp—Arg—Leu—Glu—Asn—Glu—

Ile—Arg—Glu—Thr—Lys—Asp—

Ser—Leu—Arg—Lys—Ile—Asn—Lys—

Ser—Ile—Asp—Gln—Tyr—Asp—Lys—

Tyr—Thr—Tyr—Leu—Lys—Thr—Ser(Cterminal), or for any fragment of this peptide which conserves the property of the above-mentioned peptide of activating the expression of the Ses$^h$ phenotype, in particular of stimulating the production of the above-mentioned enzymes of the strains of *B. subtilis*.

The conditions under which the active fragments can be identified have already been illustrated above.

Preferably, the DNA fragment according to the invention is characterized by the nucleotide structure extending between the positions 768 and 905 of FIG. 3.

The invention also relates to DNA sequences in which the above-mentioned fragments are preceded by sequences for regulating the expression of the sequence coding for the above-mentioned polypeptide and followed by nucleotide sequences composed of the terminator elements of transcription. These elements may consist of the sequences for regulation and/or termination which are associated with the DNA fragment defined above in the natural genes of *B. licheniformis*. For this reason, the invention relates to any DNA sequence of larger dimension derived from the Sau3A1 fragment of 3.5 kb mentioned above and which does not contain a nucleotide sequence coding for all or part of an alkaline protease, this sequence also containing the sequence coding for the polypeptide capable of inducing the Ses$^h$ phenotype as well as the nucleotide sequences comprising the elements of regulation of the expression and/or the elements of termination of transcription of the latter.

In particular, the invention relates to DNA sequences comprising the fragment of 561 base pairs bounded by the positions 353 and 914 of the 1.4 kb sequence of FIG. 3, which can be isolated from the genome of *B. licheniformis*.

The invention relates more particularly to any fragment of the genome of a *Bacillus licheniformis* contained in the sequence of about 1,400 nucleotides of the nucleic acid of FIG. 3 and comprising the sequence coding for the polypeptide activator of the Ses$^h$ phenotype.

The nucleic acid fragment of the type in question can be constituted by the total sequence of 1,400 nucleotides of the nucleic acid of FIG. 3. However, it has been observed that the total sequence is not necessary.

As examples of fragments in conformity with the invention and satisfying the set of conditions which have been recalled in the definition cited above of the DNA fragment according to the invention, mention will be made of:

the polynucleotide bounded by terminal nucleotides corresponding to the nucleotides situated at the positions 353 and 914 respectively of FIG. 3, which comprises the promoter of transcription, the ribosome binding site, the structural gene for the sacQ$_L$ polypeptide of 46 amino acids.

the polynucleotide bounded by terminal nucleotides corresponding to the nucleotides situated at the positions 353 and 1012 respectively of FIG. 3, which includes the terminator of transcription in addition to the polynucleotide just mentioned, the polynucleotide containing the fragment bounded by terminal nucleotides corresponding to the positions 686 to 914 respectively of FIG. 3, and comprising, in addition, upstream of the said fragment a sequence sufficiently long to also include the endogeneous promoter which makes transcription in the cell host possible, in particular by *B. subtilis*.

any polynucleotide comprising a fragment contained between the nucleotide 353, on the one hand, and the nucleotide 905 and containing, in addition, downstream of the said fragment a sequence sufficiently long for it to include the homologous termination sequences of the gene of *B. licheniformis*.

any polynucleotide bounded on the one hand by a nucleotide included between the positions 1 to 353 and, on the other hand, by a nucleotide included between the positions 905 and 914 of FIG. 3.

any polynucleotide bounded, on the one hand, by a nucleotide included between the positions 1 to 353 and, on the other hand, by a nucleotide included between the positions 1012 and 1400 of FIG. 3.

The invention also relates to any recombinant nucleic acid containing any fragment of the above-mentioned type coding for the sacQ$_L$ polypeptide activator of the Ses$^h$ phenotype associated with fragments of nucleic acid which are heterologous with respect to the said fragment, i.e. fragments of nucleic acid having sequences foreign to that of the sequences of nucleic acid which surround the fragment defined above in the genome of B. licheniformis.

For this reason, the invention relates to any recombinant DNA containing a sequence coding for the sacQ$_L$ polypeptide activator of the Ses$^h$ phenotype associated respectively with a promoter of transcription recognized by B. subtilis and/or a terminator of transcription which is heterologous with respect to the DNA of B. licheniformis, this promoter and/or this terminator being nonetheless recognized by the polymerases of B. subtilis.

In this respect, the invention relates more particularly to the recombinant DNAs consisting of vectors containing a DNA fragment according to the invention in one of their sites which is not essential for their replication, in particular of the plasmid type, which can be replicated in B. subtilis and which can give rise in it to the expression of the sequence coding for the sacQ$_L$ polypeptide activator of the Ses$^h$ phenotype.

Advantageously, the above-mentioned heterologous promoter of transcription is chosen from among those, the activity of which can be induced. In the subsequent discussion such promoters will be called inducible promoters. As an example of an inducible promoter, mention may be made of the promoter spac (Proc. Natl. Acad. Sci. USA, 81, 439–443, (1984)) which can be induced by IPTG (isopropyl $\beta$-D-thiogalactoside).

Preferred vectors according to the invention are bifunctional vectors capable of being replicated in both E. coli and B. subtilis, in particular the shuttle vectors pHV33 or pMK4 described, respectively in Plasmid: 6, 193-201 (1981) and Gene: 29, 21-26 (1984), the ligation of the sequences of the invention to the genomes of these vectors then being performed at the Bam HI sites of the latter. pMK4 is illustrative of the multicopy plasmids which also form part of the invention, i.e. plasmids capable of being multiplied in a large number of copies in the host cell.

The vectors according to the invention are thus preferably chosen from among those making possible the induction of over-production of the sacQ$_L$ polypeptide in the host cell, such as the above-mentioned multicopy plasmids including an inducible promoter.

The invention also relates to the sacQ$_L$ polypeptide of 46 amino acids defined above and the active peptide fragments which derive from it.

This polypeptide according to the invention is defined as the activator of the expression of one or more target genes in a given organism.

The carboxyl terminal portion of the primary structure of the activator can be modified without too substantial a loss of its activity, in particular the last seven amino acids may be replaced by other residues.

The invention relates to a procedure for the production of secreted enzymes which includes the transformation of B. subtilis by means of the plasmids indicated above, the growth of the transformed cells of B. subtilis in an appropriate medium and the recovery of the said enzymes from the culture medium.

Such a procedure according to the invention makes possible the over-production by strains of B. subtilis of a large number of extracellular enzymes, principally the alkaline protease but also the levansucrase, carboxymethylcellulase, $\beta$-glucanase, lichenase, xylanase, $\alpha$-amylase.

The invention also relates to a procedure for the production of a polypeptide specified by a strain of B. subtilis, the genome of which has been modified by the insertion of a nucleotide sequence coding for the said polypeptide, which comprises the transformation of the strain of B. subtilis indicated above by means of vectors making possible the overproduction of an activator of the Ses$^h$ phenotype in the cells of B. subtilis, the growth of the said transformed cells in an appropriate medium, and the recovery of the said polypeptide from the culture medium.

Of the above-mentioned activators of the Ses$^h$ phenotype, mention will be made in particular of the polypeptides sacQ$_L$, sacQ$_S$, sacQ$_A$ and the polypeptide of 60 amino acids derived from B. natto mentioned above.

Preferentially, the vectors used for the implementation of such a procedure are the above-mentioned plasmids which make possible the overproduction of sacQ$_L$ in B. subtilis.

Generally speaking, any naturally occurring enzymes secreted by B. subtilis is first translated in the form of a polypeptide precursor, the amino acid sequence of which corresponds to that of a signal peptide followed by that of the secreted enzyme. At the time of cellular secretion, only the mature form corresponding to the enzyme itself is secreted outside of the cell.

The modification of the genome of B. subtilis, prior to the transformation of the latter according to the procedure of the invention, is preferentially carried out in a manner such that the above-mentioned genome comprises a nucleotide sequence coding for a specific polypeptide preceded by a nucleotide sequence, designated hereafter by "signal ID sequence", coding for a signal peptide, the role of which is to enable the said polypeptide to be secreted, the said signal sequence being itself preceded by a nucleotide sequence consisting of a target sequence previously defined and a promoter of the expression of such a DNA fragment.

Thus, the replacement of a sequence of DNA coding for the intracellular production of an enzyme in B. subtilis by a sequence of DNA coding for a specific polypeptide, or the replacement of a sequence of DNA coding for the secretion of an enzyme in B. subtilis by a sequence of DNA coding for a signal peptide connected to the specific peptide makes it possible to obtain the said polypeptide in its final form secreted directly by the cell host, after this latter has been transformed by a plasmid containing a sequence of DNA coding for a polypeptide activator of the Ses$^h$ phenotype according to the procedure of the invention.

The strain of B. subtilis used for the implementation of such a procedure is advantageously modified by means of a vector, in particular a plasmid, containing in one of its sites not essential for replication the DNA sequence coding for the specific polypeptide, preceded by a signal sequence, which is itself preceded by a nucleotide sequence containing a target sequence and the elements necessary to promote the expression of the signal sequence and the sequence coding for the specific polypeptide.

Another subject of the invention is a procedure for the production of a specific polypeptide by a strain of B. subtilis which comprises the transformation of the said strain of B. subtilis by means of a vector containing, in one of its sites not essential for its replication, a sequence of DNA coding for a polypeptide activator of the Ses$^h$ phenotype, and enabling the said activator to be over-produced in the cells of B. subtilis, and a sequence of DNA coding for the specific polypeptide, this latter sequence of DNA being preceded by a signal sequence which is itself preceded by a nucleotide sequence consisting of a target sequence and the elements necessary to promote the expression of the signal sequence and the sequence coding for the specific polypeptide, the growth of the said transformed cells in an appropriate medium, and the recovery of the said polypeptide from the culture medium.

Of the above-mentioned activators of the Ses$^h$ phenotype, mention will be made particularly of the polypeptides sacQ$_L$, sacQ$_S$, sacQ$_A$ and the polypeptide of 60 amino acids derived from B. natto mentioned above.

Advantageously, the above-mentioned vector comprises a sequence of DNA coding for the polypeptide activator sacQ$_L$.

Of the signal sequences used for the construction of the vectors of the invention, mention will be made in particular of the one making possible the secretion of the alkaline protease, the levansucrase, cellulase and α-amylase.

Generally speaking, any signal sequence preceding the DNA sequence coding for an enzyme by B. subtilis may be used.

Preferentially in the case where there is a risk of the specific polypeptide being degraded by the action of one or more of the enzymes secreted naturally by B. subtilis, in particular by the alkaline protease, the gene coding for such an enzyme is modified by deletion or by mutation so that the said enzyme is not secreted or secreted in a form which is inactive toward the specific polypeptide.

Advantageously, the sequence coding for the specific polypeptide in the above-mentioned vectors is preceded by the signal sequence contained in the sacB gene coding for the levansucrase in B. subtilis, and which is described in Biochem. Biophys. Res. Com.: 119, 2, 795–800 (1984), the said signal sequence being itself preceded by a DNA fragment containing on the one hand the endogenous Sau3A1-Rsa1 nucleotide sequence of 440 base pairs defined above including the sacR gene of B. subtilis and in which the target sequence is located and, on the other hand, the elements necessary for the expression of the sequences coding for the signal peptide and for the specific polypeptide.

In fact, the levansucrase is secreted by B. subtilis when the latter is in the exponential phase of growth whereas the other enzymes are secreted by B. subtilis in the stationary phase. Thus the insertion of a sequence of DNA coding for a specific polypeptide downstream from the endogenous signal sequence of the levansucrase makes it possible to obtain the said polypeptide free from the other enzymes secreted by B. subtilis when the culture of this latter is stopped at the end of the exponential phase of growth.

Thus, the invention relates to a procedure for the production of a practically pure, specific polypeptide which comprises the growth of cells of B. subtilis by means of a plasmid containing, in one of the sites not essential for its replication, a sequence of DNA coding for the specific polypeptide, preceded by the signal sequence included in the sacB gene coding for the levansucrase in B. subtilis, the said signal sequence being itself preceded by a fragment of DNA containing, on the one hand, the endogenous Sau3A1-Rsa1 nucleotide sequence of 440 base pairs including the sacR gene of B. subtilis and in which the target sequence is located and, on the other hand, the elements necessary for the expression of the sequences coding for the signal peptide and for the specific polypeptide, the said cells being transformed by means of vectors permitting the over-production of an activator of the Ses$^h$ phenotype in the cells of B. subtilis preferentially the sacQ$_L$ polypeptide, the interruption of the culture at the end of the exponential phase of growth of the said cells of B. subtilis and the recovery of the specific polypeptide from the culture medium practically free of the other extracellular enzymes likely to be secreted by the cells of B. subtilis.

The invention also relates to a procedure for the production of a practically pure, specific polypeptide which comprises the growth of cells of B. subtilis modified by means of a plasmid containing, in one of the sites not essential for its replication, a sequence of DNA coding for a polypeptide activator of the Ses$^h$ phenotype, preferentially for the sacQ$_L$ activator, permitting the over-production of the said activator in the cells of B. subtilis, and a sequence of DNA coding for the specific polypeptide, this latter sequence of DNA being preceded by the signal sequence included in the sacB gene coding for the levansucrase in B. subtilis, the said signal sequence being itself preceded by a fragment of DNA containing, on the one hand, the endogenous Sau3A1-Rsa1 nucleotide sequence of 440 base pairs including the sacR gene of B. subtilis and in which the target sequence is located and, on the other hand, the elements necessary for the expression of the sequences coding for the signal peptide and for the specific polypeptide, the interruption of the culture at the end of the exponential phase of growth of the said cells of B. subtilis and the recovery of the specific polypeptide from the culture medium practically free of the other extracellular enzymes likely to be secreted by the cells of B. subtilis.

It is advantageous to use strains of B. subtilis which are carriers of the sacU$^h$ mutation, known to confer on these latter an increased capacity to produce enzymes. The introduction of a sequence of the invention in sacU$^h$ mutants of B. subtilis leads to a synergistic effect affecting the over-production of the secreted enzymes, even of a specific polypeptide in the case in which the genomes of the above-mentioned mutants have been modified by insertion of a sequence coding for the said polypeptide as has been previously described.

As examples of the specific polypeptide capable of being produced by the procedure according to the invention, mention will be made of the human interferons, the interleukins and growth hormone.

The invention also relates to the cells of B. subtilis transformed by the plasmids according to the invention containing the sequence coding for an activator of the Ses$^h$ phenotype, these latter being capable of being replicated in these cells, more especially at the time of cell division.

The invention also relates to the cells of B. subtilis which are transformed at one and the same time by a plasmid containing a sequence coding for an activator of the Ses$^h$ phenotype and by the plasmid containing the sequence coding for a specific polypeptide and for the signal peptide, preceded by a target sequence such as that described above.

Another subject of the invention is the cells of *B. subtilis* transformed by a plasmid containing a sequence coding for an activator of the Ses$^h$ phenotype and the sequence coding for a specific polypeptide and for the signal polypeptide, preceded by a target sequence, such as that described above.

These cell cultures are thus capable of producing increased quantities of enzymes and/or of the specific polypeptide. It follows quite naturally from the preceding discussion that the invention relates quite particularly to the cells of *B. subtilis* mentioned above which also carry at least one sacU$^h$ mutation.

It will of course be appreciated by the specialist that the desired polypeptides, more especially the alkaline protease or the specific polypeptide, may be purified in any known manner, for example by electrophoresis on a gel and recovery of the desired polypeptide. Recourse may also be had to any other method, for example high pressure liquid chromatography.

In the foregoing discussion, essentially only the transformation of *B. subtilis* has been mentioned. The invention is not limited to the transformation of these cells. It can also be used to stimulate the production of polypeptides in other strains already used in industry. Mention may be made, for example, of *B. licheniformis, B. amyloliquefaciens, B. stearothermophilus* and also strains of *E. coli*.

Additional characteristics of the invention will also become apparent during the description which follows of the preferred vectors and of the conditions under which they may be utilized, it being understood that this description is not to be interpreted as limiting the scope of the claims.

Study of the cloning of various fragments of DNA of the invention as well as their properties of enzyme overproduction.

1) Materials and methods
Bacterial strains and plasmids:

The bacterial strains used are *Bacillus licheniformis* (deposited with the C.N.C.M. at the Pasteur Institute in Paris under the number 71 I 001) which possesses a high activity of extracellular protease production, *B. subtilis* 512 which is a mutant of the Marburg strain (J. Appl. Bacteriol.: 33, 220–227, (1970)) deficient in neutral protease, *B. subtilis* 512ts19 possessing an additional thermo-sensitive mutation spoOA (Biochimie: 58, 109–117, (1976)), *B. subtilis* 1A510 (leuA8, arg15, thr5, recE4, stp) (J. Bacteriol.: 156, 934–936, (1983)), *B. subtilis* QB881 (sacA321, leu8, argA), *B. subtilis* QB136 (sacU32, leu8, trpC2) (Biochimie: 56, 1481–1489, (1983)), *E. coli* MC1061 (araD139, Δ(ara,leu), 7697, ΔlacX74, galU−, galK−, hsr−, hsm+, strA) (J. Mol. Biol.: 138, 179–207, (1980)) and JM83 (aro, Δlac, pro−, strA, thi, φ80, dlacZ, ΔM15) (Gene: 19, 259–268 (1982)).

The plasmid vectors are the pHV33 and the pMK4 previously mentioned, both of them being capable of being replicated in *E. coli* and in *B. subtilis*.

The modifications of structure of *E. coli* and *B. subtilis*, necessary for the transfer of the genomes of the above-mentioned plasmids to those of these bacteria, were carried out in the case of *E. coli* by the conventional procedure with calcium chloride, and in the case of *B. subtilis* by the procedure of ANAGNOSTOPOULOS and SPIZIZEN (J. Bacteriol.: 81, 741–746 (1961)).

Media and qualitative tests

Both *E. coli* and *B. subtilis* are grown in L broth (10 g of Difco Bacto Tryptone, 5 g of Difco yeast extract, 5 g of sodium chloride per liter); the SP medium is composed of 8 g/l of Difco Bacto nutrient broth, 1 mM of MgSO$_4$ and 13 mM of KCl to which are added after sterilization 2.5 μM of FESO$_4$, 500 μM CaCl$_2$ and 10 μM of MnCl$_2$.

Chloramphenicol is added at 5 μg/ml and ampicillin at 100 μg/ml. The mineral medium (MM) is composed of 60 mM of K$_2$HPO$_4$, 44 mM of KH$_2$PO$_4$, 3 mM of sodium citrate, 2 mM of MgSO$_4$, 10 uM of MnCl$_2$, 0.5 mM of CaCl$_2$ and 10 mg/L of ammonium ferric citrate (J. Bacteriol.: 81, 741–746).

The levansucrase activity is estimated by detection of the appearance of glucose with a Statzyme Glucose 50 (Worthington).

The hydrolyses of carboxymethylcellulose (Type II, Sigma), lichenan (Sigma) and xylan (Sigma) were detected by covering the culture dishes with 1% Congo Red for one hour and by washing several times with 1M NaCl until clear zones appear.

The dishes containing colonies which do not bind stably to the agar were covered with 5 ml of a solution of soft agar at 7 g/l before being stained.

The degradation of starch is detected by sublimating iodine onto the dishes.

Measurement of the activities of the neutral protease and of the alkaline protease Appropriate dilutions of culture supernatants were preincubated in the presence and in the absence of 6 mM of phenylmethanesulfonyl fluoride (PMSF). 200 μl samples were then diluted to 1 ml with a solution of 100 mM Tris/HCl (pH 8.0), 2 mM of CaCl$_2$, and 5 mg/ml of azocasein (Calbiochem) and incubated at 40° C. The reactions were stopped with the aid of 0.8 ml of 15% TCA (trichloroacetic acid). After centrifugation, 1 ml of supernatant was neutralized with 50 μl of 10N NaOH and the optical density was measured at 440 nm.

One azocasein unit corresponds to 1 μg of azocasein hydrolyzed per minute or to 0.406 Delft unit.

The protease activity sensitive to PMSF is attributed to the alkaline protease whereas the activity resistant to PMSF is due essentially to the neutral protease.

Measurement of saccharolytic activity

An aliquot of the culture supernatantsis incubated in the presence of 8% of sucrose, 50 mM KH$_2$PO$_4$ (pH 6.0) in a final volume of 0.6 ml at 37° C. The reactions were stopped by boiling. The amount of glucose liberated is measured by incubation in the presence of orthodianisidine, glucose oxidase (free of invertase activity) and peroxidase. One enzymatic unit corresponds to 1 μmole of glucose liberated per minute (Methods in Enzymol.: 8, 500–505, (1966)).

2) Results

Isolation of a plasmid responsible for the over-production of protease

The chromosomal DNA of *Bacillus licheniformis* strain 71 I 001 was partially cleaved by Sau3A1 and fragments of 3 to 5 kb were purified by electrophoresis on agarose gel.

These chromosomal fragments were ligated to those of the bifunctional vector pHV33 (*E. coli-B. subtilis*) at the dephosphorylated BamHI site and the ligation mixture was used to transform a strain of *E. coli* MC 1061. Sixteen thousand transformants containing 85% of recombinants were selected on ampicillin and chloramphenicol.

The plasmid DNA was extracted from eight groups of 2,000 colonies each, purified and used to transform competent cells of *B. subtilis* 512.

The 512 strain is deficient in activity of the neutral protease type and does not produce the characteristic halo of precipitation of casein due to the activity of the secreted protease.

Six thousand colonies resistant to chloramphenicol were tested for their activity of the protease type on dishes of casein from each of the eight groups.

Two positive clones were found in one of the groups.

The plasmid DNA was extracted from the two clones and used to transform *B. subtilis* 512.

All of the transformants obtained displayed the same characteristic halo around the colonies, thus demonstrating that the over-production of protease is linked to the presence of the plasmid in *B. subtilis*.

Analyses of the two plasmids showed that they were identical and had inserted a 3.5 kb Sau3A1 fragment of the chromosome.

One of the plasmids was named pPR4 and has been studied in more detail.

Characterization of the activity of the protease type

The plasmid pPR4 as well as the vector PHV33 were introduced by transformation into the strain 1A510 of *B. subtilis* which is deficient in recombination functions but which carries the wild-type alleles of the protease genes.

The two types of transformants obtained were grown in the SP media containing 1% casein and 5 μg/ml of chloramphenicol.

The protease activity of the culture supernatant was measured in the presence and in the absence of PMSF which specifically inhibits the serylprotease (alkaline protease).

The PMSF-resistant activity is due to the neutral protease.

As is indicated in FIG. 1, a very strong stimulation of the alkaline protease activity is produced in the presence of the plasmid pPR4, in comparison with the reference strain carrying only the vector pHV33. The maximal stimulation which is about 70 fold is obtained after 17 hours of culture.

However, the activity of the neutral protease type is stimulated to a much lower extent. The maximal increase produced is by a factor of 4 after 17 hours of culture.

After 22 hours of culture, there is no difference in neutral protease activity between the cells containing pPR4 and pHV33.

Subcloning of the fragment of 3,500 base pairs

The pPR4 plasmid which carries the 3.5 kb fragment was partially digested with Sau3A1.

The fragments obtained were subjected to electrophoresis on agarose gel and 6 zones of migration corresponding to the following fragment sizes were excised from the gel.

1.2 to 1.4 kb; 1.4 to 1.6 kb; 1.6 to 1.8 kb; 1.8 to 2.0 kb; 2.0 to 2.3 kb and 2.3 to 2.8 kb.

The DNA of each gel slice was purified by electroelution and ligated at the dephosphorylated BamHI site of the plasmid pMK4.

The vector pMK4 is a shuttle vector for *B. subtilis* and *E. coli* produced by fusion of pC194 and pUC9.

The strain *E. coli* JM83 was transformed with the ligation mixture and the plasmid- DNA was extracted from all of the transformants which had multiplied in the presence of ampicillin and chloramphenicol.

The extracted DNA was utilized to transform *B. subtilis* 512ts19 (thermo-sensitive sporulation mutant of the 512 strain), and the transformants were selected on dishes of minimal medium (MM) to which was added 2% of skimmed milk and chloramphenicol.

Colonies over-producing proteases were found for each of the six different fragment sizes selected.

A colony of *B. subtilis* over-producing protease corresponding to the DNA derived from the gel slice lying between 1.2 and 1.4 kb ligated to pMK4 was re-isolated and its plasmid was extracted and amplified in *E. coli* JM83 (pPR41).

Figure 2:
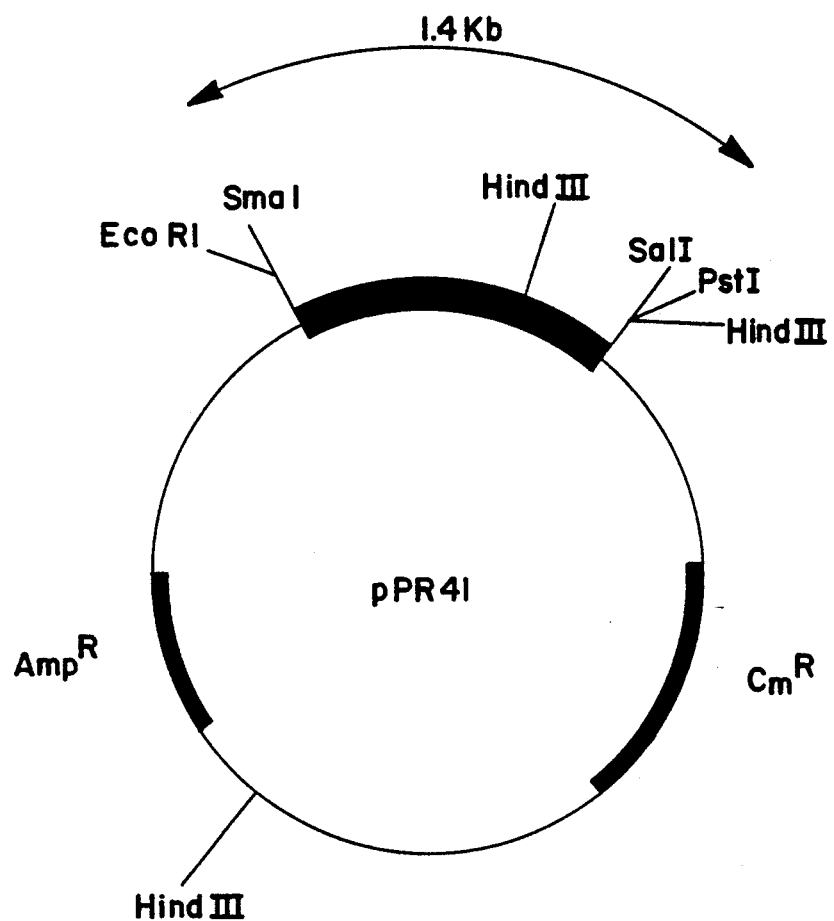
FIG. 2 shows a representation of the vector pPR41 carrying the 1.4 kb sequence of the invention, FIGS. 3A and B show the complete sequence and the restriction map of the 1.4 kb fragment, The FIGS. 4a to 4f furnish comparative results of the overproduction of different enzymes by various strains carrying a plasmid which does or does not contain a sequence of the invention.

The pPR41 plasmid contains an insertion fragment of 1.4 kb as indicated in FIG. 2.

The sequence of this 1.4 kb fragment was determined and is shown in FIG. 3.

This sequence was translated in the six possible reading-frames. None of the polypeptides obtained by translation of this sequence contains more than 101 amino acids. No homology was found between these polypeptides and the known alkaline and neutral proteases of *B. subtilis* or *B. amyloliquefaciens*. We can thus exclude the possibility that the fragment of 1,400 base pairs contains the structural gene for a protease of the subtilisin type which is composed of 379 amino acids in its precursor form, and of 274 residues in its mature form (Nucl. Ac. Res.: 13, 8913-8926, (1985)).

Characterization of the hypersecretion phenotype (Ses$^h$)

Different types of secreted enzymatic activities tested are enhanced in the presence of the plasmid pPR41. The plasmid pPR41 or the vector pMK4 is introduced by transformation into different strains of *B. subtilis* shown in Table 1.

The strains carrying the recombinant plasmid were compared to those carrying the vector alone, these strains being grown in dishes containing different degradable substrates described in the FIGS. 4a to 4f.

TABLE 1

| STRAIN | DESCRIPTION |
|--------|-------------|
| QB136 | SacU$^h$ mutant. Pleiotropic mutation which simultaneously increases the levels of levansucrase and of extracellular protease |
| QB881 | SacA$^-$ mutant. Absence of intracellular levansucrase activity. Unable to use sucrose as carbon source. |
| 512ts19 | Absence of extracellular neutral protease activity. Thermo-sensitive spoOA mutation. |
| 1A510 | Rec$^-$, Stp (stable transformation phenotype). A greater stability of the plasmids is described for this strain. |
| 5NA | SpoOA mutation. Unable to sporulate. |

Figure 4A:
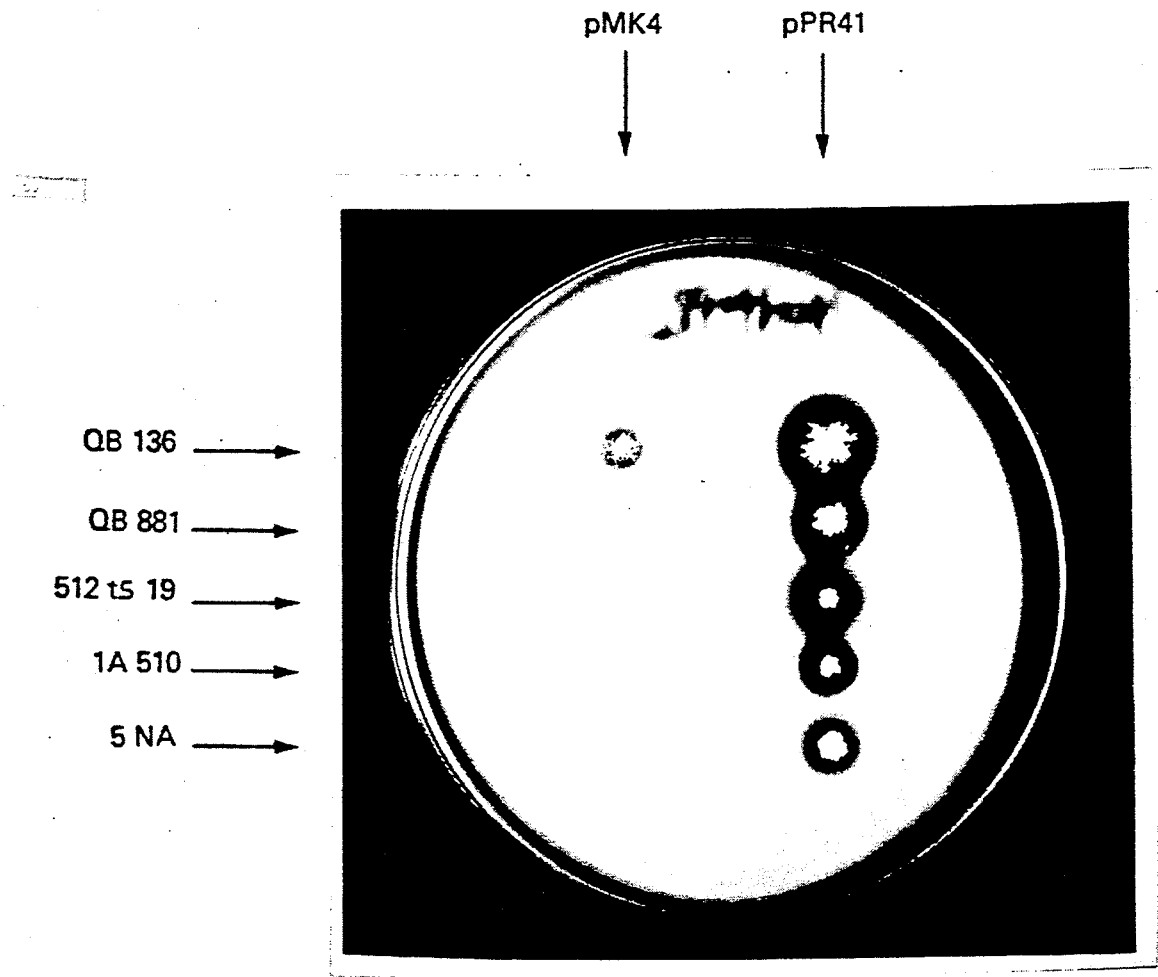

The protease activity was tested in dishes containing skimmed milk as source of carbon and nitrogen. All of the strains tested exhibit enhanced levels of activity of extracellular protease (FIG. 4a). This stimulation is independent of the chromosomal integration of the cloned fragment since it is also produced with Rec$^-$ (*B. subtilis* 1A510) or Rec$^+$ strains.

An increase of the secretion of protease is even found in spoOA mutants (*B. subtilis* 5NA), although this effect is not as marked as with the other strains. The spoOA mutants are blocked at step 0 (zero) of sporulation. Normally they exhibit very low levels of secretion and are incapable of expressing the entire set of sporulation genes. However, the presence of pPR41 does not restore the sporulation process of *B. subtilis* and consequently the function of complementation of the spoOA mutation by pPR41 can be excluded.

The strain 512ts19, carrier of a mutation at the level of the structural gene of the neutral protease, also exhibits increased secretion of proteolytic enzyme, thus confirming the results of FIG. 1 which show that it is essentially the secretion of alkaline protease which is stimulated.

A still more interesting discovery is illustrated in FIG. 4a: the plasmid pPR41 seems to stimulate the secretion of protease in a sacU$^h$ mutant (*B. subtilis* QB136). The sacU$^h$ mutation is known to be a pleiotropic mutation which increases the secretion of a large number of extracellular enzymes, including the proteases. The plasmid pPR41 thus produces a synergistic effect with the sacU$^h$ mutation on the secretion of proteases in *B. subtilis*.

The level of extracellular degradation of five other different substrates is increased by the presence of the plasmid pPR41: hydrolysis of sucrose, degradation of carboxymethylcellulose, lichenin, xylan and starch.

Figure 4B:
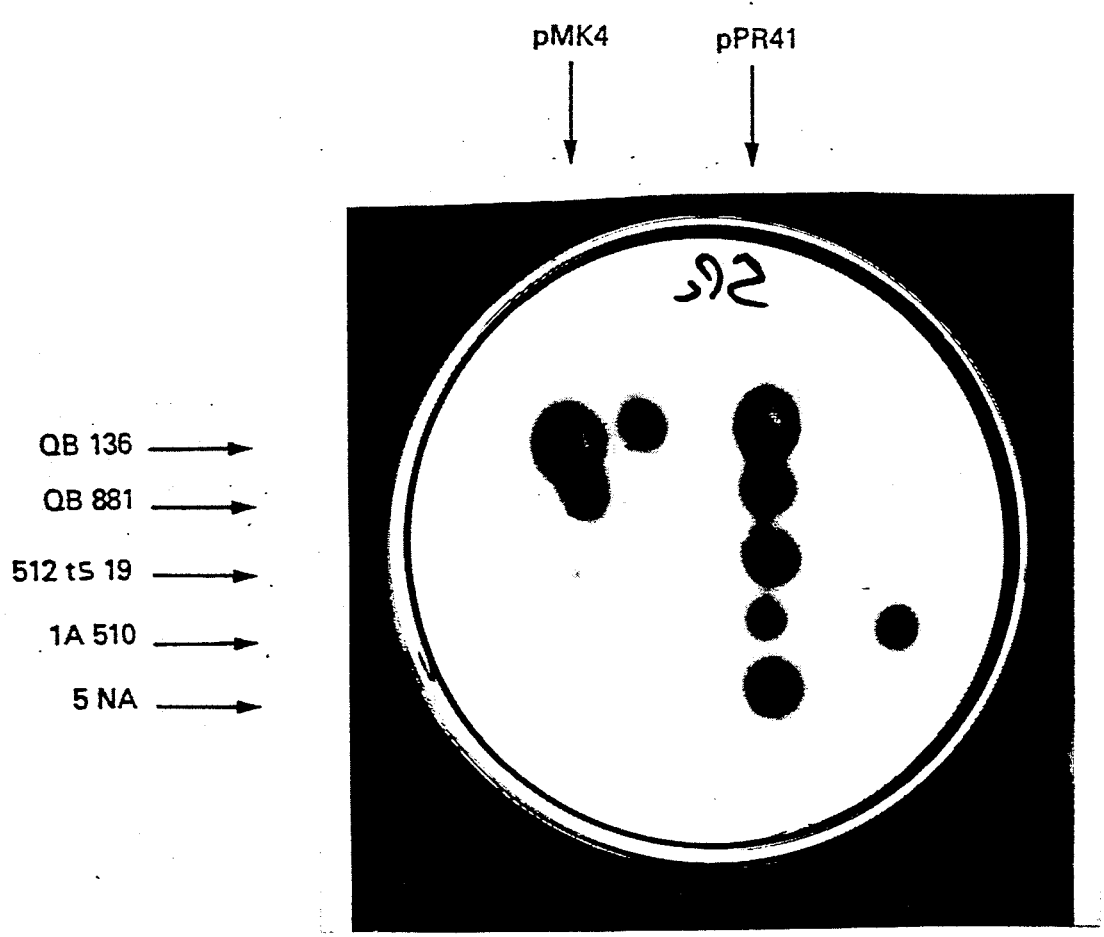
Figure 4C:
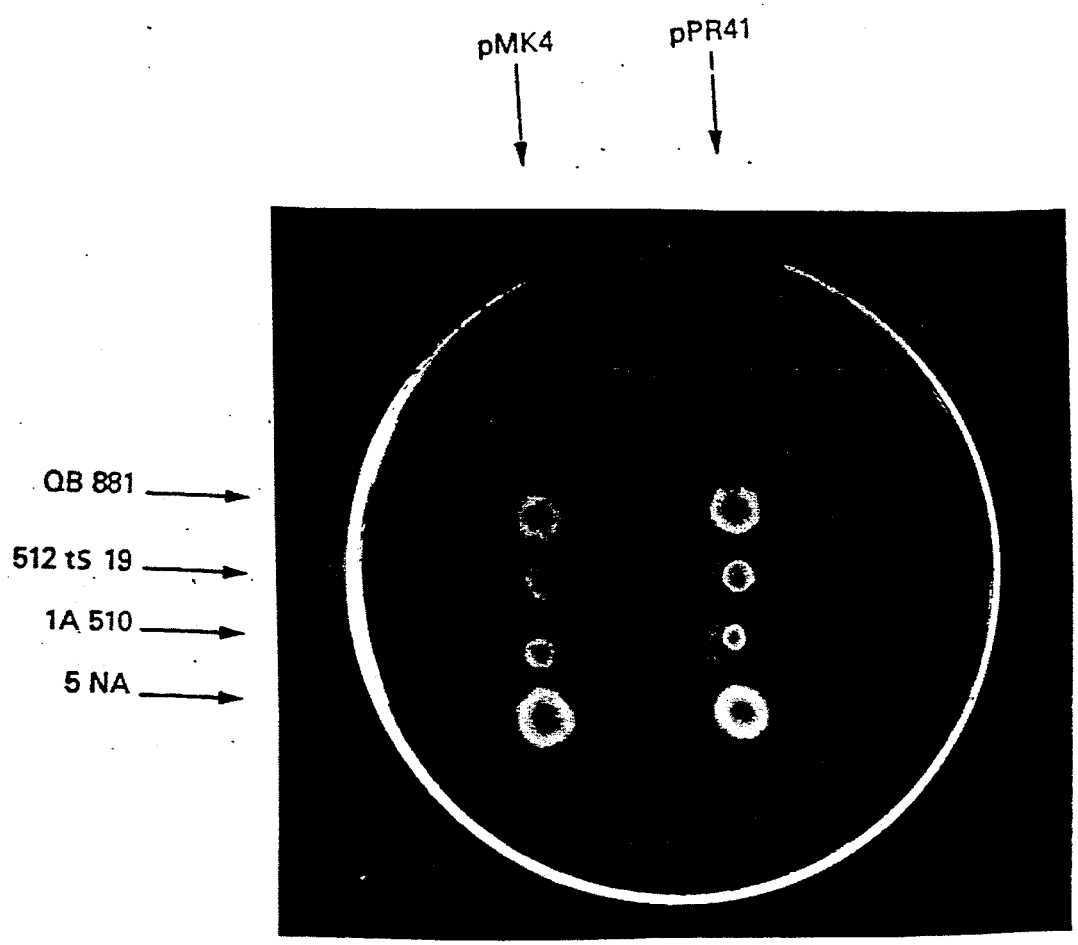

The levansucrase activity was tested by placing the colonies on a soft agar-based support containing sucrose, and by detecting the presence of glucose after 2 hours of incubation at 37° C. (FIG. 4b). The increase of the extracellular saccharolytic activity, shown in FIG. 4b, is due to the levansucrase, the synthesis of which is induced by sucrose (Microbiology. Schlessinger, D. (Ed). American Society for Microbiology, Washington D.C., pp 59–69, (1976)).

Figure 4D:
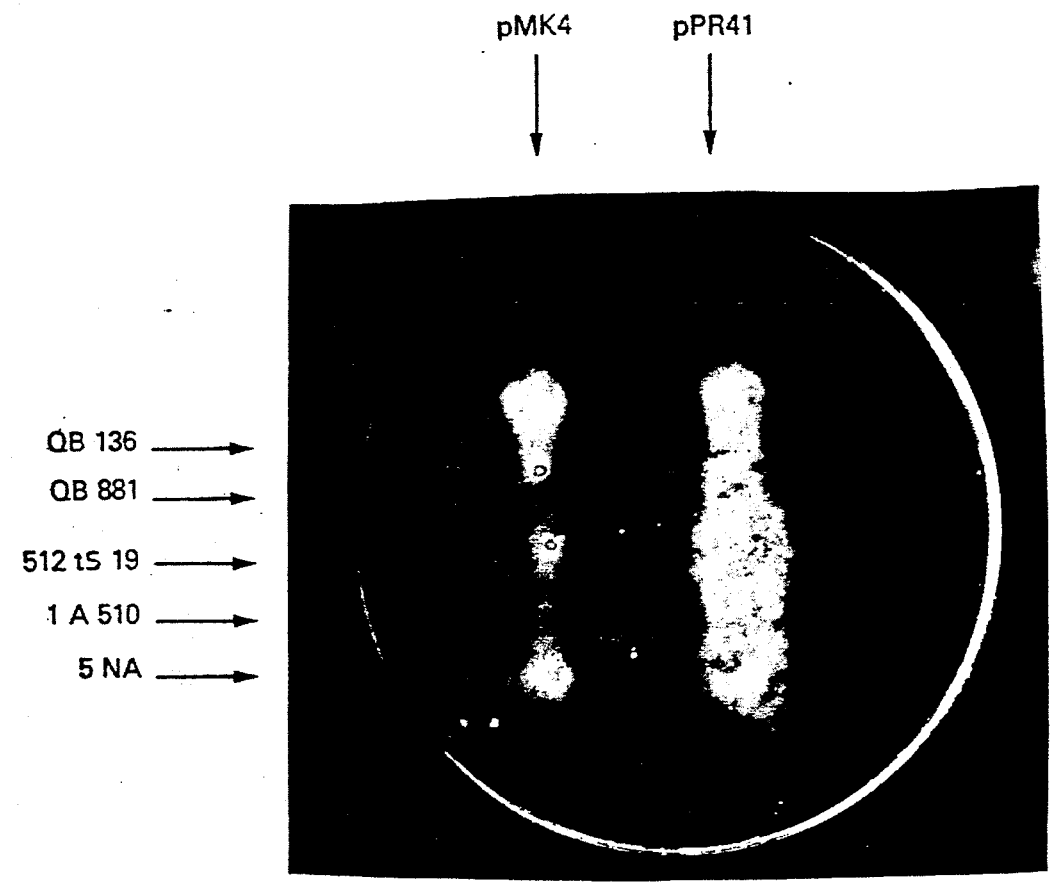

The cellulolytic activity (FIG. 4c and 4d) was tested by growing the strains in the presence of either carboxymethylcellulose (CMC), which is a β1-4 glucan (FIG. 4c) or lichenan which is a mixture of β1-3 and β1-4 glucans (FIG. 4d). Since Congo Red binds specifically to glucans of high molecular weight, the degradation of these two substrates is shown by the presence of a clear halo around the colonies. The hydrolysis of these two substrates in the presence of pPR41 indicates an increase of the secretion of β1-4 glucanase (J. Bacteriol.: 165, 612 –619, (1986) and/or β-1, 3-1, 4-glucanase (Gene: 23, 211–219, (1983). A comparable increase was produced by the strains carrying the mutation sacU$^h$.

Figure 4E:
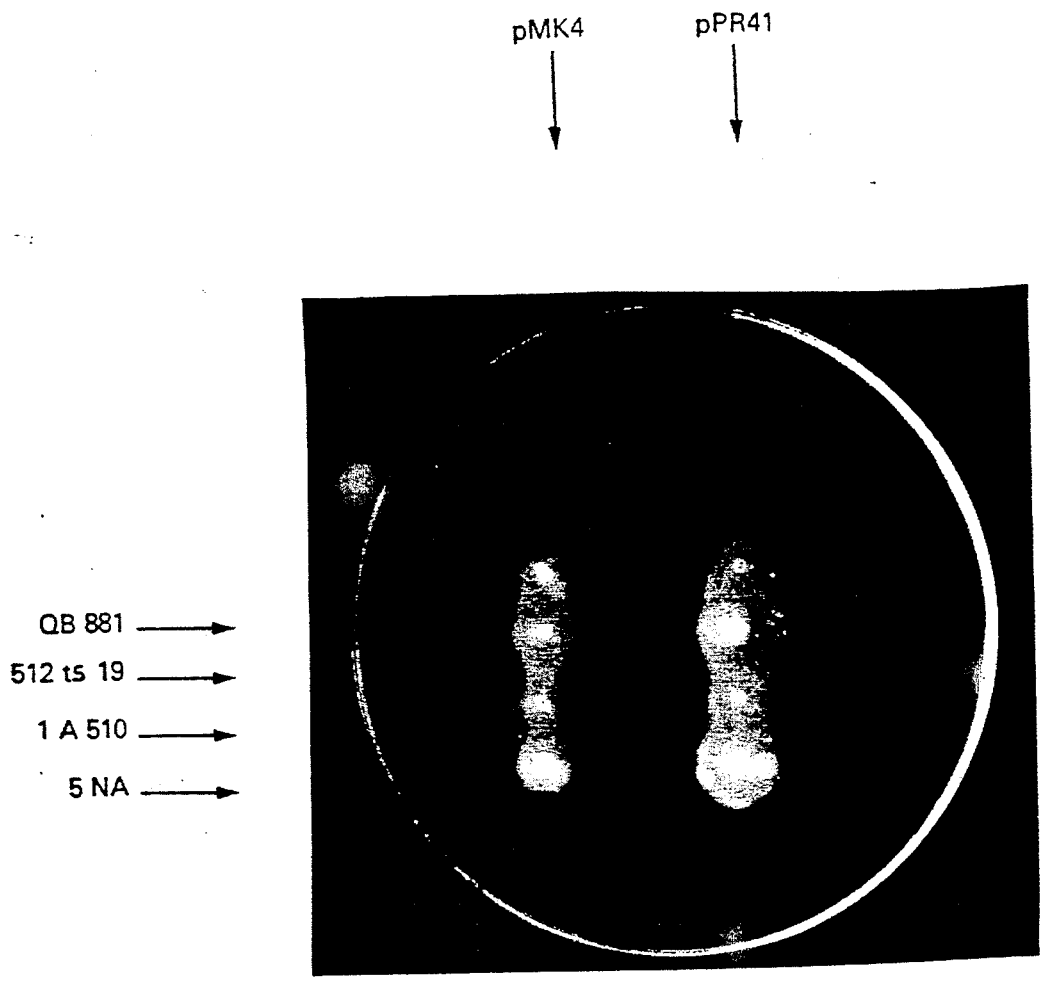

Xylanase is the fourth enzyme secreted and stimulated (FIG. 4e). The colonies grown in the presence of xylan (polymer 1–4) show larger halos of degradation in the presence of the plasmid pPR41.

Figure 4F:
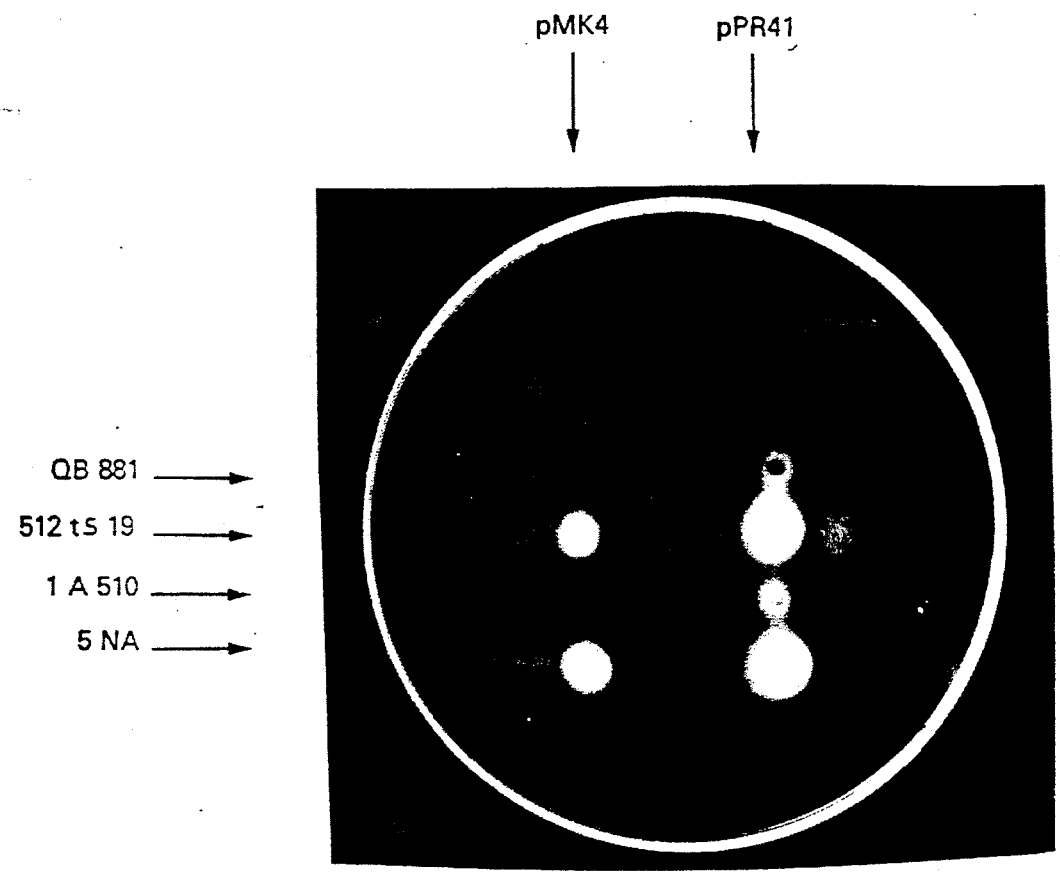

The secretion of a fifth type of extracellular degradative enzyme is increased (FIG. 4f). The strains grown in the presence of starch as sole carbon source exhibit larger halos of degradation when pPR41 is present. However, the increase was not as marked as it was for the four other extracellular activities.

Subcloning of the fragment of 1,400 bp

In order to be able to identify the smallest fragment of DNA capable of inducing hypersecretion in *B. subtilis*, the fragments obtained after deletion with Bal31 and used for the sequencing of a single-stranded phage M13 were transferred to the bifunctional plasmid pMK4.

Figure 5:
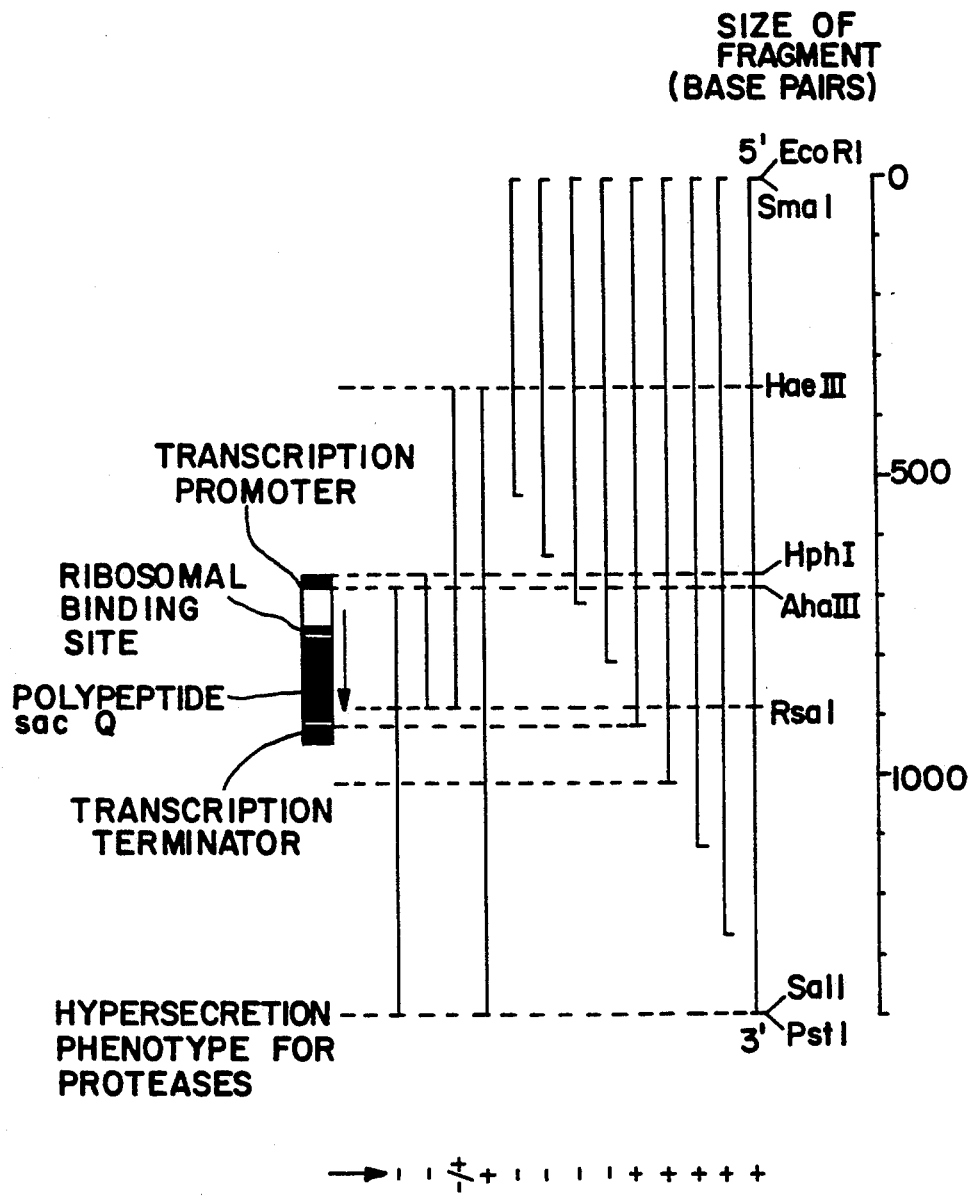
FIG. 5 shows the steps of subcloning of a 1.4 kb fragment.

The plasmids containing the fragments progressively deleted from the 3' end were introduced into the *B. subtilis* strain 1A510 and the protease type of activity secreted was visualized on solid media based on skimmed milk. The results are shown in FIG. 5.

The phenotype of hypersecretion is given by the fragment deleted from the 3' end upto position 914 (the fragment having lost the last 489 nucleotides) and is lost when the deletion is extended to position 805, a further 109 base pairs toward the 5' end.

From this it can thus be concluded that the fragment of 109 base pairs contained between the two points of deletion carries all or part of the fragment of DNA which produces the phenotype of hypersecretion in *B. subtilis*.

Suitable restriction sites have thus been used to reduce still further the size of the fragment of DNA from the 5' end.

A fragment of 353 base pairs can be deleted from the 5' side since the fragment HaeIII-PstI (position 353–1400) continues to induce the hypersecretion of protease. It has been concluded from this that the sequence responsible for hypersecretion is contained between the position 353 (HaeIII site) and the position 914 (Bal31 deletion). The last 29 nucleotides cannot be deleted from this fragment of 561 base pairs without partial loss of the phenotype. In fact, the subcloning of the fragment HaeIII-RsaI leads to a over-production of protease slightly diminished compared with the initial fragment. On the other hand, the last 109 nucleotides are essential, since their deletion leads to the total loss of the phenotype Prt$^h$.

However, these 109 nucleotides do not appear to be sufficient since the fragment AhaIII (685)-PstI (1,400) does not contain the information necessary for the induction of hypersecretion.

It is thus concluded that the size of the fragment producing the Ses$^h$ phenotype is less than 561 bp (HaeIII, 353-deletion 914) but larger than 228 bp (AhaIII, 686-deletion 914).

Figure 6:
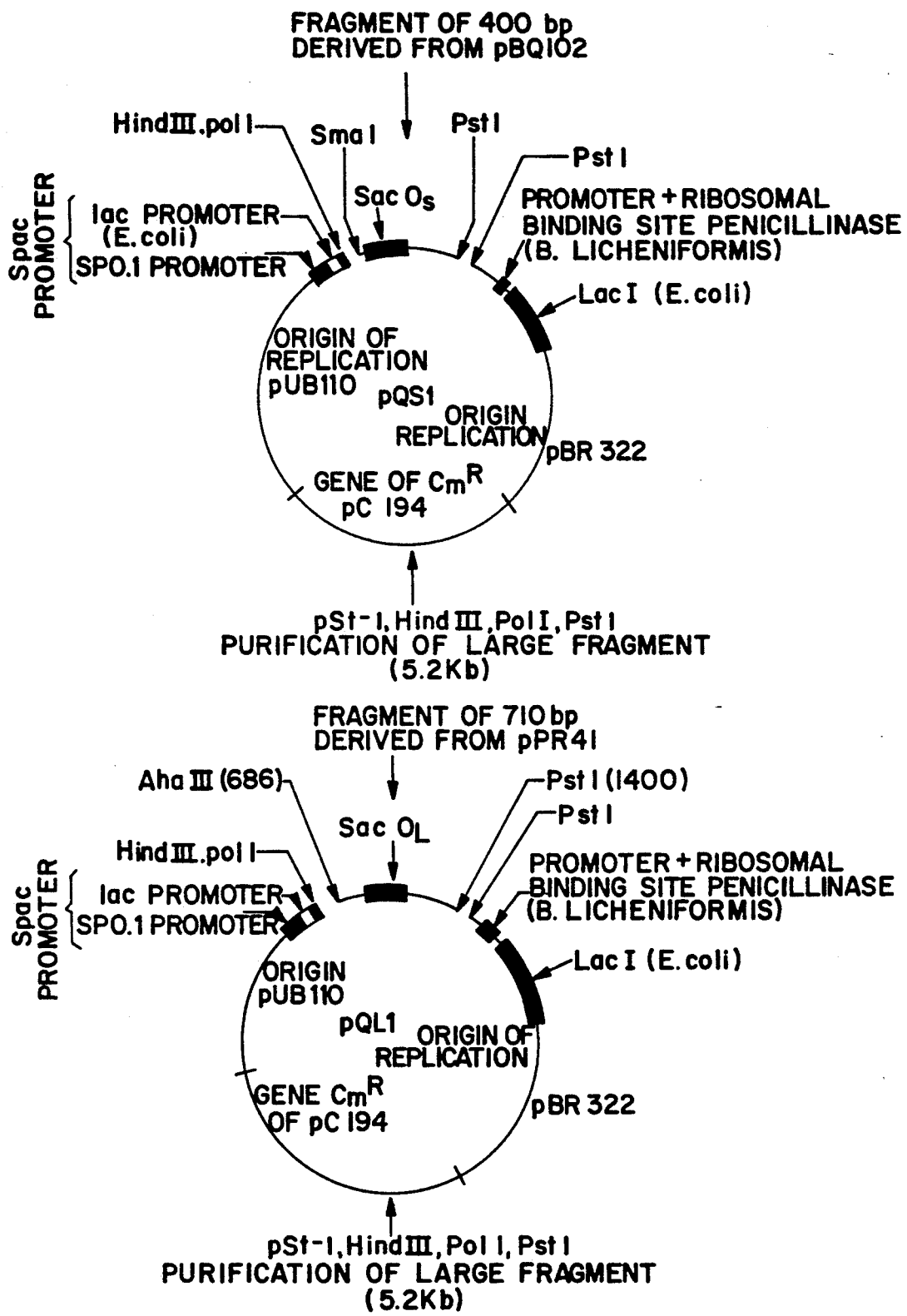
FIG. 6 shows representations of the plasmids pQL1 and pQS1 containing the $sacQ_L$ and $sacQ_S$ genes, respectively, under the control of the same inducible spac promoter, and which are defined on page of this text.

Identification and characterization of the polypeptide responsible for the Ses$^h$ phenotype The fragment AhaIII (686) PstI (1,400) was cloned under the control of a promoter recognized by *B. subtilis* in the vegetative phase of growth and inducible by IPTG (spac. promoter, Proc. Natl. Acad. Sci. U.S.A., 81, 439–443 (1984)). The plasmids pQL$_1$ and pQS$_1$ containing respectively the genes coding for sacQ$_L$, under the control of the same inducible spac promoter, are shown in FIG. 6, is their construction is more particularly detailed in the legend to this figure at the end of this Chapter 2.

The results in Table 2 show that the secretion of alkaline protease and levansucrase is induced specifically by IPTG in *B. subtilis* 1A510. This result, combined with the subcloning data, shows that a product of transcription and/or translation derived from the fragment of 228 bp (AhaIII, 686, deletion 914) is sufficient to produce the Ses$^h$ phenotype.

TABLE 2

Measurement of the extracellular activity of levansucrase and the alkaline protease

| Receptor strain | Plasmid | Description of the construction | Levansucrase units/mg × $10^3$ | | Alkaline protease azocasein units/ml sensitive to PMSF | |
|---|---|---|---|---|---|---|
| | | | − IPTG | + IPTG | − IPTG | + IPTG |
| | pMK4 | control vector | <20 | | 29 | |
| | pBQ1 | pMK4 + sacQ$_S$ | 200 | | 240 | |
| | pPR41 | pMK4 + sacQ$_L$ | 1100 | | 450 | |
| 1A510 | pSI1 | spac promoter (control) | <20 | <20 | 49 | 49 |
| | pQS1 | spac promoter + sacQ$_S$ | <20 | 200 | 40 | 67 |
| | pQL1 | spac promoter + sacQ$_L$ | <20 | 1300 | 41 | 290 |
| QB136 | pMK4 | control vector | 600 | | 490 | |
| (sacU$^h$) | pBQ1 | pMK4 + sacQ$_S$ | 600 | | 370 | |
| | pPR41 | pMK4 + sacQ$_L$ | 1100 | | 670 | |

This suggests the intervention of a polypeptide encoded by this fragment. It does indeed contain an open reading frame coding for a peptide of 46 residues preceded by a sequence typical for ribosomal binding ($\Delta G = -20.4$ Kcal/mole, FIG. 3) and terminated by a sequence characteristic of the termination of transcription ($\Delta G = -24.2$ Kcal/mole).

This peptide shows significant homology with the product of the sacQ gene of B. subtilis (J. Bacteriol., 166, 113-119) and B. amyloliquefaciens (J. Bacteriol., 3, 85-96). The polypeptide SacQ$_L$ of B. licheniformis has the same size of 46 amino acids as its homologue sacQ$_S$ of B. subtilis (FIG. 7). Nonetheless, 15 residues are different in B. licheniformis, including an insertion and a deletion. Seven of the 15 changes bring about a change in the polarity of the amino acid. Thus, the polypeptide sacQ$_L$ can be distinguished by its primary structure from the polypeptide sacQ$_S$ and also from the polypeptide sacQ$_A$ (B. amyloliquefaciens), which contains only four different amino acids when compared with sacQ$_S$, only two of which involve a change in polarity.

This distinction is also reflected in the intensity of the phenotype of hypersecretion. Table 2 shows the protease and levansucrase activities produced by B. subtilis 1A510 carrying the gene sacQ$_L$ or sacQ$_S$ on a vector present in multiple copies. The gene sacQ$_S$ of B. subtilis was cloned in the same manner as sacQ$_L$. Fragments larger than 3 kb derived from a partial Sau3A1 digestion of the chromosomal DNA of B. subtilis 168 were linked to the BamHI site of pMK4 and introduced into B. subtilis 168 after amplification in E. coli JM83. A hyperproducing protease strain contained the plasmid pBQ1. This plasmid contains an insertion of 2.9 kb at the BamHI site and expresses the Ses$^h$ phenotype similar to that produced by pPR41. The size of the insertion was reduced to 0.4 kb by a method similar to subcloning of pPR4: partial Sau3A1 digestion of pBQ1 and selection of sizes of 0.2-0.5 kb. The sequence of this fragment of 0.4 kb was determined. It is strictly identical with the sequence published for sacQ$_S$.

Table 2 shows that the presence of the gene sacQ$_L$ in multiple copies in the strain 1A510 stimulates the activity of the levansucrase secreted 5 times more than the gene sacQ$_S$ under the same conditions. As for the alkaline protease activity (sensitive to PMSF), it is stimulated twice as much by the gene from B. licheniformis as by the gene from B. subtilis. This stimulation can become up to three times better for longer times of culture (40 hours). The sacQ$_L$ gene thus produces the phenotype of hypersecretion (Ses$^h$) in B. subtilis in a more efficacious manner than the sacQ$_S$ gene. This increased efficacity may be due to the nature of the polypeptide itself or to an increase in the amount of this polypeptide produced in B. subtilis.

The results in Table 2 show that the primary sequence of the polypeptide sacQ$_L$ plays a cardinal role in the expression of the Ses$^h$ phenotype. In fact, when the two genes sacQ$_L$ and sacQ$_S$ are placed under the control of the same spac promoter inducible by IPTG (see constructions FIG. 6), the levansucrase activity is stimulated 6 times more by sacQ$_L$ than it is by sacQ$_S$. The alkaline protease activity is stimulated about 10 times more by the expression of the gene from B. licheniformis.

The alkaline protease activity is stimulated less when the genes sacQ$_L$ and sacQ$_S$ are under the control of the spac promoter than when under the control of their own promoter (Table 2). It thus has to be admitted that the regulation of the expression of the sacQ polypeptide is also important for the expression of the Ses$^h$ phenotype. Now we know, on the one hand, from the results of subcloning in FIG. 5 and those in Table 2 that the transcription promoter must be located on the fragment of 333 base pairs demarcated by the HaeIII (353) and AhaIII (386) sites. On the other hand, the site for the beginning of transcription has been determined by "S1 mapping" in B. subtilis (J. Bacteriol., 166, 113-119 (1986)). By homology, the supposed position for the beginning of transcription in B. licheniformis is the nucleotide 695 (FIG. 3 and FIG. 8). The "−10" region with respect to this start of transcription as well as the "−35" region has a sequence which resembles that of a transcription promoter. An example of a promoter (P43) of the vegetative phase recognized "in vitro" by the RNA polymerase containing the factor $\sigma^{43}$ is given for comparative purposes (J. Biol. Chem., 259, 8619-8625, (1984)). FIG. 8 shows the structure of this potential promoter compared in the different strains of Bacillus. The "−35" sequence is conserved in all of the strains whereas the "−10" sequence is variable. The first nucleotide of the "−10" sequence is important. In fact, the substitution of a C by a T leads to the Ses$^h$ phenotype in the SacQ$^h$ mutant of B. subtilis (J. Bateriol., 166, 113-119, (1986)). This same mutation is conserved in B. amyloliquefaciens and B. licheniformis, which both possess better capacities of secretion than B. subtilis. In the protease hyperproducing B. licheniformis, an additional mutation of C into A at the third nucleotide of the "−10" sequence is found.

Synergistic effect of sacQ on the sacU$^h$ mutation

Table 2 presents a comparison of the effects of the presence of the genes sacQ$_L$ and sacQ$_S$ in multiple copies in a strain of B. subtilis QB136 which carries the sacU$^h$ mutation. The presence of the sacQ$_S$ gene does not increase the level of levansucrase activity and diminishes that of alkaline protease of the strain QB136 whereas the presence of the sacQ$_L$ gene increases these levels of activity about two-fold.

All of the levansucrase activities presented in Table 2 were carried out in the presence of sucrose. In the absence of sucrose, the activity is less than 0.02 U/mg (result not shown).

In other words, the induction of the expression of the sacB gene by sucrose seems to be a phenomenon of its over-expression caused by the presence of several copies of the sacQ gene.

The carboxyl terminal portion of the sacQ polypeptide is hypervariable

The HaeIII (353)-RsaI (885) fragment was subcloned at the SmaI site of the pMK4 vector and a partial phenotype of hyperproduction of protease was obtained (FIG. 5). From the known sequences of the vector pMK4 and of the gene sacQ$_L$ the synthesis of a hybrid polypeptide can be predicted in which the last seven amino acids of sacQ$_L$ are replaced by 11 totally different residues derived from the translation of a sequence of pMK4. This hybrid sacQ polypeptide containing a modified carboxyl terminal expresses, in consequence, a reduced activity compared with the intact polypeptide. This suggests that the last seven residues contribute to and finally the sacR and sacB sequences located downstream from the Sau3A1 site (position 1) of sacR.

Table 3 presents the measurement of the resistance to kanamycin of the *B. subtilis* QB4058 strain. The minimal concentration of kanamycin necessary to inhibit the growth of the strain *B. subtilis* QB4058 carrying the plasmids indicated was determined according to the method described in Antibiot. Chemother. 9, 307–311 (1959). Several dilutions (1:10$^2$, 1:10$^3$, and 1:10$^4$) of a culture of QB4058 in exponential growth in a PAB broth (Penassay Broth marketed by DIFCO) containing chloramphenicol were placed on Mueller-Hinton agar containing kanamycin and, when indicated, 2% sucrose. The phenotype for the secretion of levansucrase (still designated by the abbreviation Lvs) is estimated by detection on the plate: Lvs$^-$ corresponds to the absence of a halo of saccharolytic activity; Lvs$^+$ and Lvs$^-$ correspond to the presence of a small and large halo of saccharolytic activity, respectively.

Table 3 shows that the resistance to kanamycin is conferred on the strain QB4058 by the simultaneous presence of multiple copies of sacQ$_S$ and sucrose. sacQ$_L$ confers a better resistance to the antibiotic than does sacQ$_S$, confirming the preliminary results relating to the greater efficacy of the polypeptide derived from *B. licheniformis*.

| PLASMID PRESENT IN THE STRAIN QB4058 | MINIMAL CONCENTRATION OF KANAMYCIN (ug/ml) REQUIRED TO INHIBIT GROWTH | | PHENOTYPE FOR THE SECRETION OF LEVANSUCRASE | |
| --- | --- | --- | --- | --- |
| | − SUCROSE | + SUCROSE | − SUCROSE | + SUCROSE |
| pMK4 | 8 | 16 | Lvs$^-$ | Lvs$^+$ |
| pBQ1 (pMK4 + sacQs) | 8 | 32 | Lvs$^-$ | Lvs$^h$ |
| pPR41 (pMK4 + sacQl) | 8 | 128 | Lvs$^-$ | Lvs$^h$ | the conferent of an optimal structure on the polypeptide but are not essential for its activity.

This result is compatible with the fact that the last residues of the sacQ polypeptide are variable in *B. licheniformis* (FIG. 7).

Nonetheless, a fused polypeptide which only contains the first twelve amino acids of the SacQ polypeptide followed by 19 amino acids derived from reading the pMK4 vector is totally lacking in activity (deletion 805).

Identification of a target of the sacQ gene

In order to identify a target of the sacQ gene, the inventors carried out a fusion of nucleotide sequences in which the regulator site (sacR) of the sacB gene coding for the levansucrase is used to control the expression of the structural gene of a cytoplasmic protein, the 3', 5''-aminoglycoside phosphotransferase (aph3') of *Streptococcus faecalis* (Gene., 23, 331–341 (1983)). This gene confers resistance to kanamycin when it is expressed in *B. subtilis*.

Figure 9:
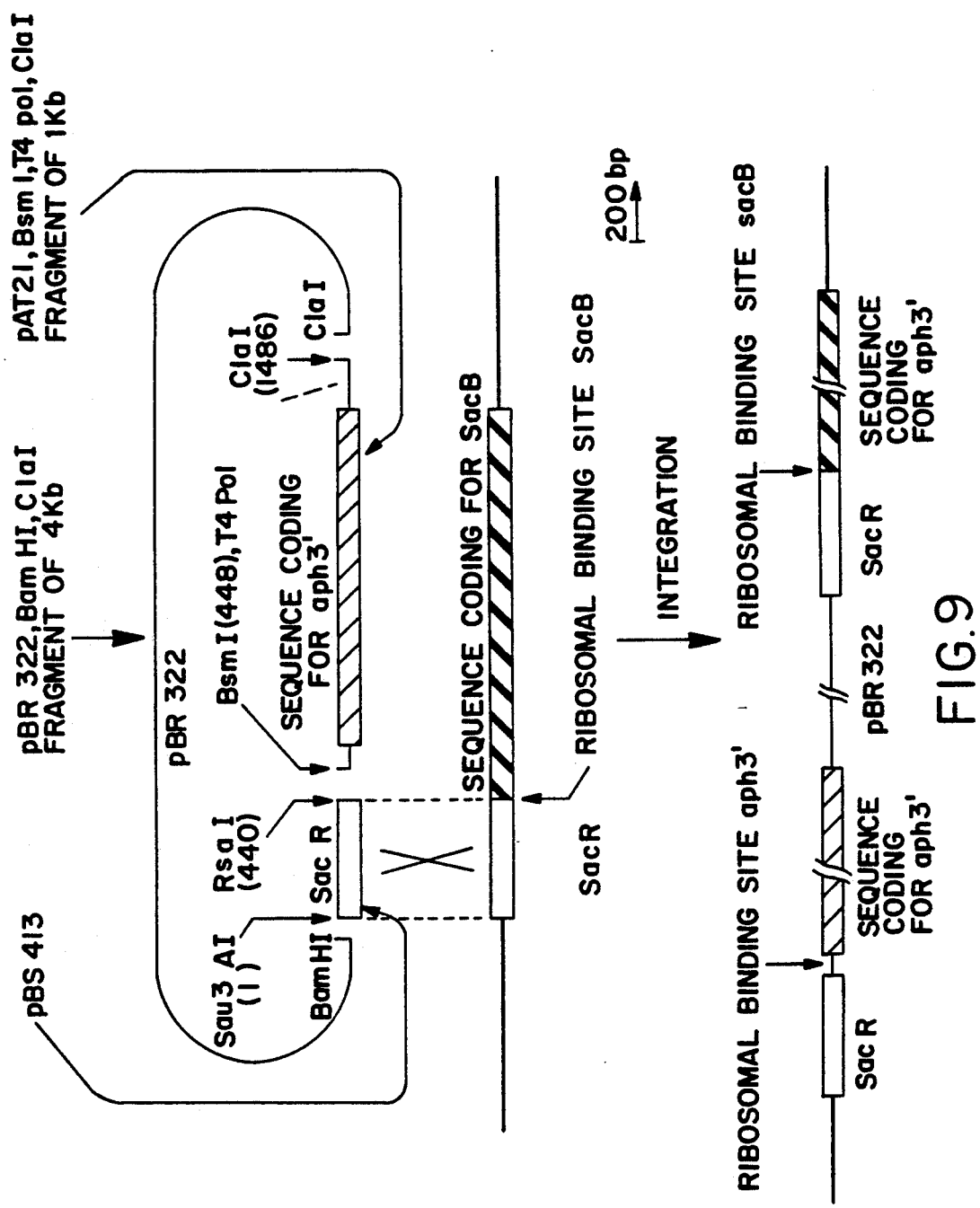
FIG. 9 presents the construction of the fusion gene sacR-aph3′.

FIG. 9 shows the way in which the strain QB4058 was constructed.

After integration by homologous recombination, the chromosomal sequences remain theoretically intact up to the end of the sacR locus at the level of the RsaI site 440 (nucleotide numbered as described in Mol. Gen. Genet., 200, 220–228 (1984)) which is located just before the ribosomal binding site of the sacB gene.

Thus sacR is followed directly by the ribosomal binding site of the aph3'gene, the sequence coding for the aph3' and the termination signals, the pBR322 sequence Thus, the expression of the aph 3' gene is activated by overproduction of the sacQ polypeptide.

It may also be concluded from this experiment that the activation site is a fragment of DNA situated upstream from the RsaI site (440) which includes sacR. The activity of secretion of levansucrase by the strains resistant to kamamycin was tested so as to determine at what distance upstream from the RsaI site the target of sacQ is located.

Table 3 shows that the level of secretion of levansucrase is increased in the presence of plasmids carrying the sacQ gene.

The target of sacQ must thus be located downstream from the sau3A1 site. In consequence, the sacQ target seems to be located in the Sau3AI-RsaI fragment situated in the neighbourhood of the sequence coding for the levansucrase.

Examples of the construction of a plasmid containing the signal sequence of levansucrase a) Construction of the plasmid pBS610

The DNA extracted from a strain of *B. subtilis* 168 was partially digested with HindIII.

After electrophoresis on polyacrylamide gel, the fragments of 4 kb were cloned in the plasmid pUC8, described in Gene, 19, 259–268 (1982), which can only replicate in *E. coli*. The recombinant plasmid was isolated from the clone synthesizing levansucrase. This latter was detected by its action on sucrose, which is converted into glucose and polymers of fructose by the action of levansucrase.

The plasmid isolated was digested with EcoRI and BamHI. The BamHI-EcoRI fragment which was isolated contains a HindIII-EcoRI fragment of about 2 kb, the restriction map of which is shown in FIG. 10. This fragment contains the signal sequence of the levansucrase.

The above-mentioned BamHI-EcoRI fragment was recombined in a new plasmid with the BamHI-EcoRI fragment obtained from pBR322, after digestion of this latter with the enzymes BamHI and EcoRI, and containing the elements responsible for the replication of pBR322 in *E. coli*.

A HindIII-HindIII fragment of about 2.9 kb, consisting of the plasmid pC194, and containing the elements enabling the said plasmid pC194 to replicate in *B. subtilis*, was inserted into the recombinant plasmid previously obtained, more particularly at the level of the HindIII site contained in the BamHI-EcoRI fragment containing the sequence signal of levansucrase, in order to produce, finally, the plasmid pBS610 represented schematically in FIG. 11. The plasmid pBS610, the genome of which is about 8.9 kb, can replicate in *E. coli* and in *B. subtilis*.

The plasmid pC194 can be obtained from the plasmid pHV33. A strain of *E. coli* transformed by pHV33 was deposited in the National Collection of Cultures of Micro-Organisms (N.C.C.M.) at the Pasteur Institute, France, under the number I-191.

b) Construction of the plasmid pBS620

A HindIII-EcoRI fragment containing the signal sequence of the levansucrase was obtained by digestion in the presence of the endonucleases EcoRI and HindIII of the modified phage λ obtained by insertion at the level of the BamHI sites of the phage λ-EMBL3 described in J. Mol. Biol., 170, 827–842 (1983), of products of partial Sau3A1 digestion of the DNA of the strain *B. subtilis* 2010 carrying a mutation sacR$^c$ and secreting levansucrase continuously. The above-mentioned modified phage contains the above-mentioned sacR$^c$ promoter. A strain of *E. coli* containing this modified phage was deposited with the N.C.C.M. under the number I-314.

The EcoRI-HindIII fragment of 2 kb containing the signal sequence of the levansucrase and the locus sacR$^c$ were recombined with the EcoRI-HindIII fragment of about 4.3 kb isolated from pBR322 and containing the elements enabling the plasmid pBR322 to replicate in *E. coli*. The plasmid obtained was again digested with HindIII and recombined with the above-mentioned fragment of 2.9 kb derived from the plasmid pC194 in order to produce the plasmid pBS620 shown schematically in FIG. 12. The pBS620 can also replicate in *B. subtilis* and *E. coli*.

The plasmids pBS610 and pBS620 can then be modified by the insertion of a sequence of DNA coding for a specific polypeptide, C, preferably following the signal sequence, and by the insertion upstream from the said signal sequence of a sequence of DNA containing a target sequence according to the invention and the elements making possible the expression of the signal sequence and the sequence of DNA coding for the specific polypeptide by the cell host.

Generally speaking, the modification of the plasmids containing a signal sequence so that they include a sequence of DNA coding for a specific polypeptide can be carried out by any method which can be devised by the specialist depending, in particular, on the various enzymes and restriction sites chosen.

The modified plasmids thus obtained can be used to transform *B. subtilis* so that this latter produces and excretes the specific polypeptide. This transformation can, for example, be carried out according to the method described in J. Bacteriol., 114, 273–286 (1973). The cells containing plasmids and resistant to the antibiotic can be selected on SP agar plates supplemented with chloramphenicol (5 μg/ml).

The transformed cells of *B. subtilis* can be detected, for example, by using antibodies prepared beforehand and directed against the specific polypeptide. The cells of the colonies detected can then be isolated and used to prepare cultures of cells synthesizing and secreting the specific polypeptide into the culture medium. The polypeptide can then be isolated from the culture medium by any suitable method.

The legends corresponding to the figures illustrating the preceding experiments and observations are as follows:

FIG. 1

*Bacillus subtilis* 1A510 containing the vector pHV33 or the plasmid pPR4 are placed in culture at 37° C. in SP medium supplemented with chloramphenicol at 5 μg/ml and casein to 1%. The protease activity of the supernatants is measured in the presence or absence of PMSF at the times indicated.

FIG. 2

Plasmid pPR41. Amp$^R$ and Cm$^R$ indicate the genes of resistance to ampicillin and chloramphenicol, respectively. This plasmid contains an origin of replication of *E. coli* and an origin of replication of *B. subtilis*.

Sequence of the fragment of 1,400 base pairs. The points of Bal31 deletion are indicated by ᄂ. The sites recognized by the restriction enzymes are underlined as is a palindromic sequence suggesting the structure of a terminator of transcription. The probable start of transcription is indicated by →. The complementary sequence to the 3' end of the 16s ribosomal RNA of *B. subtilis* is indicated by double underlining.

FIG. 4a

Qualitative test for the proteolytic activity secreted by *B. subtilis*. The strains are grown for three days on Petri dishes containing MM medium supplemented by chloramphenicol at 5 μg/l and skimmed milk powder (Difco) to 2%.

FIG. 4b

Qualitative tests for the saccharolytic activity in *B. subtilis*. After growth overnight in SP medium containing chloramphenicol, the plates are sprayed with 1 ml of 50% sucrose. After 1½ hours of incubation at 37° C., the glucose liberated is visualized by revelation with Statzyme.

FIG. 4c

Qualitative tests for the degradation of carboxymethylcellulose, the colonies are placed in culture overnight in L medium containing chloramphenicol. After being overlaid with soft agar containing 1% of carboxymethylcellulase, they are incubated for 4 hours at 37° C. before staining with Congo Red.

FIG. 4d

Qualitative tests for the degradation of lichenans. The colonies are placed in culture for 2 days in Mm medium supplemented with (NH$_4$)$_2$SO$_4$ to 2%, a hydrolysate of casein to 0.01%, chloramphenicol to 5 μg/ml and lichenan to 0.4% before being stained with Congo Red.

FIG. 4e

Qualitative test for the degradation of xylans. The colonies are placed in culture at 37° C. for 2 days on MM medium supplemented with (NH$_4$)$_2$ SO$_4$ to 2%, a hydrolysate of casein to 0.01%, chloramphenicol to 5 µg/ml and xylan to 0.4% before being stained with Congo Red.

FIG. 4f

Qualitative tests for the degradation of starch. The colonies are placed in culture for 3 days on MM medium supplemented by (NH$_4$)$_2$ SO$_4$ to 2%, a hydrolysate of casein to 0.01%, chloramphenicol to 5µg/ml and starch to 1%. The dishes are stained with iodine.

FIG. 5

Subcloning of the fragment of 1,400 base pairs.

FIG. 6

Construction of plasmids containing sacQ$_L$ and sacQ$_S$ under the control of the same inducible spac promoter.

The plasmids pQL1 and pQS1 are constructed by insertion of fragments carrying the sacQ$_L$ and sacQ$_S$ genes lacking their promoter into the plasmid pSI-1 at the HindIII site after annealing with the DNA polymerase (polI). The plasmid pSI-1 contains the spac promoter introduced at the EcoRI site of pIQ45 (Proc. Natl. Acad. U.S.A., 81, 439–443 (1984)). The position of the AhaIII site and PstI indicated for pQL1 corresponds to the positions of the sequence in FIG. 3. The plasmid pBQ102 results from the subcloning of a fragment of 400 base pairs at the BamHI site of pMK4. This fragment was obtained by partial digestion of the plasmid pBQ1 by Sau3A1. The sequence of this fragment shows that it begins at the Sau3A1 site corresponding to position 47 of the published sacQ sequence of *B. subtilis* (J. Bacteriol., 166, 113–119 (1986)). The beginning of the sequence of the fragment inserted into pQS1 is thus

G-G-G-G-A-T-C-T-T-T-C-A-A-A ...

The Sau3A1 site (G-A-T-C) underlined corresponds to the Sau3A1 site shown in FIG. 3.

FIG. 7

Comparison of the sacQ polypeptides of *B. subtilis* (B. s.), *B. amyloliquefaciens* (B. a.) and *B. licheniformis* (B. a.) and *B. licheniformis* (B. l.). A continuous line indicates residues identical to those of *B. subtilis*. The different amino acids are indicated for *B. amyloliquefaciens* and *B. licheniformis*. A deletion is indicated by XXX and an insertion by ⌒. The sequences for B. s. and B. a. are those published (J. Bacteriol., 166, 113–119, (1986)).

FIG. 8

Comparison of the structures of possible promoters in the different strains of Bacillus. The following sequences are published: *B. subtilis* SacQ$^h$, sacQ+: J. Bacteriol., 166, 113–119, (1986); *B. amyloliquefaciens*: J. Biotechnol., 3, 85–96, (1985); *B. subtilis*P43: J. Biol. Chem., 259, 8619–8625, (1984).

The abbreviations B. s, B. a and B. l correspond to *B. subtilis*, *B. amyloliquefaciens* and *B. licheniformis*, respectively.

FIG. 9

Construction of the fused gene sacR-aph3'. The plasmid used for the integration by homologous recombination was constructed by in vitro ligation of the 3 fragments sacR, aph3' and sacB. The numbering of the nucleotides is identical with that published in Mol. Gen. Genet., 200, 220–228 (1985) for sacR, and in Gene., 23, 331–341 (1983) for aph3'. The plasmid pBS413 was cloned as follows. A product of partial digestion by HindIII of the chromosomal DNA of *B. subtilis* 168 was ligated at the HindIII site of pUC 8. A strain of *E. coli* transformed by pBS413, in which was inserted a fragment containing sacB of 4.1 kb derived from a partial digestion with HindIII, possesses a saccharolytic activity. A EcoRI fragment of 2.0 kb containing sacR and the beginning of sacB was purified from pBS413 and used to isolate the Sau3A1-Rsa1 fragment of 440 base pairs containing sacR. The plasmid pAT21 has been described in Gene., 23, 331–341 (1983). The pBR322 derivative containing the fused gene was introduced into the chromosome of *B. subtilis* 168 by homologous integration. A strain containing the fused gene (QB4058) was selected on plates of kanamycin containing 2% sucrose. The integration site, determined by pBS1 transduction experiments, corresponds to the locus sacB.

FIG. 10

Restriction map of the HindIII-EcoRI fragment derived from the strain of *B. subtilis* 168. This fragment contains at the level of the thicker line in the figure the signal sequence of the levansucrase as well as the first 112 nucleotides of the gene coding for the levansucrase.

FIG. 11

Plasmid pBS610.

The parts indicated by the arcs of the circle a and b (about 2 kb and 20 base pairs, respectively) are derived from the BamHI-EcoRI fragment comprising the HindIII-EcoRI fragment of FIG. 10, the part indicated by the arc of the circle c (about 2.9 kb) is derived from the plasmid pC194 and the part d (about 4 kb) is derived from pBR322.

FIG. 12

Plasmid pBS620

The different parts of pBS620 are indicated in the figure with the references to the plasmids or DNAs from which they have been obtained.

The strain of *B. subtilis* QB4058 was deposited with the N.C.C.M. at the Pasteur Institute in Paris under the number I-587.

The strain of *B. subtilis* transformed by the plasmid pPR41 was deposited with the N.C.C.M. at the Pasteur Institute in Paris under the number I-579.

Any sequence possessing the capacity to hybridize with the active sequences described above and capable of inducing the same type of activity is included in the framework of protection conferred on the invention by the claims which follow.

Thus, any sequence which could be distinguished from those which have been described more particularly only by a certain number of mutations which do not alter the stimulating properties of the mutant are to be considered as sequence equivalents more specifically identified in the claims.

We claim:

1. An isolated fragment of DNA derived from *B. licheniformis* which codes for a polypeptide having the following sequence:

(Nterminal)Met—Glu—Lys—Gln—Gln—

Ile—Glu—Glu—Leu—Lys—Gln—

Leu—Leu—Trp—Arg—Leu—Glu—Asn—Glu—

Ile—Arg—Glu—Thr—Lys—Asp—

Ser—Leu—Arg—Lys—Ile—Asn—Lys—

Ser—Ile—Asp—Gln—Tyr—Asp—Lys—

-continued

Tyr—Thr—Tyr—Leu—Lys—Thr—Ser(Cterminal), or for any fragment of this polypeptide which conserves the activity of the above-mentioned polypeptide of activating the expression of the Ses$^h$ phenotype in *B. subtilis*.

2. Fragment of DNA according to claim 1 encoding a polypeptide demarcated by the terminal nucleotides corresponding to the nucleotides located at the positions 768 and 905, respectively, of FIG. 3.

3. Fragment of DNA derived from a Sau3A1 fragment of 3.5 kb of *B. licheniformis* not including the nucleotide sequence coding for an active alkaline protease, and comprising the isolated fragment of DNA according to claim 1, downstream of a nucleotide sequence containing the elements for the regulation of the expression of this latter.

4. Fragment of DNA according to claim 3 wherein the nucleotide sequence containing the elements for the regulation of the expression of the isolated fragment of DNA is that associated with this latter in the natural genome of *B. licheniformis*.

5. Fragment of DNA according to claim 3 including any polynucleotide demarcated, on the one hand, by a nucleotide included between the positions 1 to 353 and, on the other, by a nucleotide included between the positions 905 and 914 of FIG. 3.

6. Fragment of DNA according to claim 3 wherein the isolated fragment of DNA is upstream from a nucleotide sequence comprising the terminator elements for the transcription of this latter.

7. Fragment of DNA according to claim 6 wherein the nucleotide sequence comprising the terminator elements for the transcription of the fragment of the isolated DNA is that associated with this latter in the natural genome of *B. licheniformis*.

8. Fragment of DNA according to the claim 6 comprising any polynucleotide demarcated on the one hand by a nucleotide included between the positions 1 to 353 and, on the other, by a nucleotide included between the position 1012 and 1400 of FIG. 3.

9. Recombinant nucleic acid including the fragment of DNA according to claim 1 inserted into a nucleic acid heterologous with respect to the said fragment of DNA.

10. Recombinant nucleic acid according to claim 9 including a plasmid having said fragment of DNA at one of the sites which is not essential for its replication.

11. Plasmid according to claim 10 capable of transforming *B. subtilis*.

12. Plasmid according to claim 11 including a shuttle plasmid between *B. subtilis* and *E. coli*.

13. Plasmid according to the claim 10 possessing an origin of replication conferring on its the property of being able to replicate in multiple copies in a cell host.

14. Plasmid according to the claim 10 including an inducible promoter.

15. Cells of *B. subtilis*, producers of increased amounts of extracellular enzymes including a plasmid according to claim 10 which is capable of replicating in said cells.

16. Cells of *B. subtilis* according to claim 15 further including a sacU$^h$ mutation.

17. Procedure for the production of extracellular enzymes comprising the steps of placing in culture the cells of *B. subtilis* according to claim 15 and recovering said enzymes from the culture medium.

18. Vector for the transformation of *B. subtilis* including at one of its sites which is not essential for replication the sequence of DNA according to claim 1.

19. Vector according to claim 18 which is a plasmid for the transformation of *B. subtilis*.

20. Cells of *B. subtilis* transformed by the plasmid according to claim 19.

21. Cells of *B. subtilis* according to claim 20 further including a sacU$^h$ mutation.

22. Procedure for the production of a specific polypeptide comprising the steps of placing in culture the cells of a strain of *B. subtilis* according to claim 20 and recovering said polypeptide from the culture medium.

23. Procedure for the production of a specific polypeptide comprising the steps of placing in culture the cells of *B. subtilis* according to claim 20, and interrupting the culture at the end of the exponential phase of growth of said cells of *B. subtilis*, and recovering the specific polypeptide from the culture medium.

24. Plasmid according to claim 19 wherein the sequence of DNA coding for the polypeptide is downstream of the signal sequence indicated in the sacB gene coding for levansucrase in *B. subtilis*, said signal sequence being downstream of a fragment of DNA containing
  a) the Sau 3A1-Rsa 1 440 base pair fragment comprising the sacR gene of *B. subtilis*, said 440 base pair fragment being a target of an activator of the expression of the Ses$^h$ phenotype and
  b) the elements necessary for the expression of the sequences coding for the signal peptide for the polypeptide.

25. Polypeptide activator of the expression of the Ses$^h$ phenotype of the following structure:

(Nterminal)Met—Glu—Lys—Gln—Gln—

Ile—Glu—Glu—Leu—Lys—Gln—

Leu—Leu—Trp—Arg—Leu—Glu—Asn—Glu—

Ile—Arg—Glu—Thr—Lys—Asp—

Ser—Leu—Arg—Lys—Ile—Asn—Lys—

Ser—Ile—Asp—Gln—Tyr—Asp—Lys—

Tyr—Thr—Tyr—Leu—Lys—Thr—Ser(Cterminal),

* * * * *